United States Patent
Grüner et al.

(10) Patent No.: US 10,934,436 B2
(45) Date of Patent: Mar. 2, 2021

(54) EFFECT PIGMENTS HAVING HIGH TRANSPARENCY, HIGH CHROMA AND HIGH BRILLIANCY, METHOD FOR THE PRODUCTION AND USE THEREOF

(71) Applicant: Eckart GmbH, Hartenstein (DE)

(72) Inventors: Michael Grüner, Auerbach (DE); Günter Kaupp, Neuhaus (DE); Ralph Schneider, Lauf (DE)

(73) Assignee: Eckart GmbH

(*) Notice: Subject to any disclaimer, the term of this patent is extended or adjusted under 35 U.S.C. 154(b) by 199 days.

(21) Appl. No.: 15/536,206

(22) PCT Filed: Dec. 21, 2015

(86) PCT No.: PCT/EP2015/080859
§ 371 (c)(1),
(2) Date: Jun. 15, 2017

(87) PCT Pub. No.: WO2016/097416
PCT Pub. Date: Jun. 23, 2016

(65) Prior Publication Data
US 2017/0349756 A1  Dec. 7, 2017

(30) Foreign Application Priority Data
Dec. 19, 2014 (EP) .................... 14199293

(51) Int. Cl.
*C09C 1/00* (2006.01)
*A61K 8/02* (2006.01)
(Continued)

(52) U.S. Cl.
CPC .......... *C09C 1/0024* (2013.01); *A61K 8/0262* (2013.01); *A61K 8/19* (2013.01);
(Continued)

(58) Field of Classification Search
None
See application file for complete search history.

(56) References Cited

U.S. PATENT DOCUMENTS 3,087,828 A * 4/1963 Linton .................. B82Y 30/00
                                              106/417
3,711,308 A   1/1973 Brand et al.
(Continued)

FOREIGN PATENT DOCUMENTS

CA    2180669 A1   1/1997
CN    1312840 A    9/2001
(Continued)

OTHER PUBLICATIONS

Byk-Gardner; Katalog; "Qualitatskontrolle tor Lacke and Kunststoffe" 2011/2012, pp. 97-98. In English and German.
U.S. Appl. No. 62/004,007, filed May 28, 2014.

*Primary Examiner* — Colleen P Dunn
*Assistant Examiner* — Ross J Christie
(74) *Attorney, Agent, or Firm* — The Webb Law Firm

(57) ABSTRACT

The invention relates to a transparent effect pigment which includes a non-metallic platelet-shaped substrate and a coating applied thereto, wherein the coating has a spacer layer. The invention further relates to a method for the production, as well as the use, of the transparent effect pigment.

51 Claims, 4 Drawing Sheets

(51) Int. Cl.
  *A61K 8/19* (2006.01)
  *A61K 8/25* (2006.01)
  *A61Q 1/10* (2006.01)
  *A61Q 19/00* (2006.01)
(52) U.S. Cl.
  CPC .................. *A61K 8/25* (2013.01); *A61Q 1/10* (2013.01); *A61Q 19/00* (2013.01); *C09C 1/0009* (2013.01); *C09C 1/0015* (2013.01); *A61K 2800/262* (2013.01); *A61K 2800/43* (2013.01); *C01P 2002/52* (2013.01); *C01P 2004/03* (2013.01); *C01P 2004/51* (2013.01); *C01P 2004/52* (2013.01); *C01P 2004/61* (2013.01); *C01P 2006/63* (2013.01); *C01P 2006/64* (2013.01); *C01P 2006/65* (2013.01); *C09C 2200/102* (2013.01); *C09C 2200/1004* (2013.01); *C09C 2200/1033* (2013.01); *C09C 2200/1087* (2013.01); *C09C 2200/20* (2013.01); *C09C 2200/301* (2013.01); *C09C 2200/302* (2013.01); *C09C 2200/304* (2013.01); *C09C 2200/305* (2013.01); *C09C 2200/401* (2013.01); *C09C 2200/407* (2013.01); *C09C 2220/106* (2013.01)

(56) References Cited

U.S. PATENT DOCUMENTS

| | | | |
|---|---|---|---|
| 4,086,100 A | 4/1978 | Esselborn et al. | |
| 4,744,832 A | 5/1988 | Franz et al. | |
| 5,017,207 A | 5/1991 | Walkinson et al. | |
| 5,273,576 A | 12/1993 | Sullivan et al. | |
| 5,302,199 A | 4/1994 | Prengel et al. | |
| 5,344,486 A | 9/1994 | Mainz | |
| 5,607,504 A | 3/1997 | Schmid et al. | |
| 5,624,486 A | 4/1997 | Schmid et al. | |
| 5,753,317 A | 5/1998 | Sullivan et al. | |
| 5,759,257 A | 6/1998 | Ambrosius et al. | |
| 5,958,125 A | 9/1999 | Schmid et al. | |
| 6,000,804 A | 12/1999 | Kimura | |
| 6,045,914 A | 4/2000 | Sullivan et al. | |
| 6,113,873 A | 9/2000 | Tunashima et al. | |
| 6,129,784 A | 10/2000 | Ikuta et al. | |
| 6,261,469 B1 | 7/2001 | Zakhidov et al. | |
| 6,280,520 B1 | 8/2001 | Andes et al. | |
| 6,290,766 B1 | 9/2001 | DeLuca, Jr. et al. | |
| 6,485,556 B1 | 11/2002 | DeLuca, Jr. | |
| 6,517,763 B1 | 2/2003 | Zakhidov et al. | |
| 6,569,529 B1 | 5/2003 | Phillips et al. | |
| 6,579,355 B1 | 6/2003 | Schmidt et al. | |
| 6,596,070 B1 | 7/2003 | Schmidt et al. | |
| 6,599,355 B1 | 7/2003 | Schmidt et al. | |
| 6,648,957 B1* | 11/2003 | Andes ...................... A61K 8/11 106/404 | |
| 6,656,259 B2 | 12/2003 | Pfaff et al. | |
| 6,692,561 B1 | 2/2004 | Schoen et al. | |
| 6,719,838 B2 | 4/2004 | Heider et al. | |
| 6,777,085 B1* | 8/2004 | Argoitia ................ C09C 1/0015 428/328 | |
| 6,840,993 B2 | 1/2005 | Schmidt et al. | |
| 7,169,222 B2 | 1/2007 | Bruckner et al. | |
| 7,241,503 B2 | 7/2007 | Noguchi | |
| 7,303,622 B2 | 12/2007 | Loch et al. | |
| 7,413,599 B2 | 8/2008 | Henglein et al. | |
| 7,604,862 B2 | 10/2009 | Ambrosius et al. | |
| 7,993,443 B2 | 8/2011 | Fuller et al. | |
| 7,993,444 B2 | 8/2011 | Fuller et al. | |
| 8,007,583 B2 | 8/2011 | Fuller et al. | |
| 8,383,531 B2 | 2/2013 | Fujiwara et al. | |
| 8,383,532 B2 | 2/2013 | Fujiwara et al. | |
| 8,500,901 B2 | 8/2013 | Rueger et al. | |
| 8,585,818 B1* | 11/2013 | Jones ..................... C09C 1/0015 106/31.9 | |
| 8,715,407 B2 | 5/2014 | Schumacher et al. | |
| 8,728,226 B2 | 5/2014 | Schumacher et al. | |
| 8,728,227 B2 | 5/2014 | Schumacher et al. | |
| 8,728,228 B2 | 5/2014 | Schumacher et al. | |
| 9,051,471 B2 | 6/2015 | Gruner et al. | |
| 9,663,661 B2 | 5/2017 | Kaupp et al. | |
| 10,597,544 B2 | 3/2020 | Mathias et al. | |
| 2002/0104461 A1 | 8/2002 | Schmidt et al. | |
| 2002/0169244 A1 | 11/2002 | Ostertag et al. | |
| 2003/0005859 A1 | 1/2003 | Andes et al. | |
| 2003/0039836 A1 | 2/2003 | Pfaff et al. | |
| 2003/0097965 A1 | 5/2003 | Heider et al. | |
| 2003/0205170 A1 | 11/2003 | Schmidt et al. | |
| 2003/0209169 A1 | 11/2003 | Andes et al. | |
| 2004/0003758 A1 | 1/2004 | Bruckner et al. | |
| 2004/0052743 A1 | 3/2004 | Schmidt et al. | |
| 2004/0139889 A1 | 7/2004 | Zimmermann et al. | |
| 2004/0144023 A1 | 7/2004 | Bruckner et al. | |
| 2004/0166316 A1 | 8/2004 | Noguchi | |
| 2004/0180010 A1 | 9/2004 | Andes et al. | |
| 2006/0027140 A1 | 2/2006 | Kniess et al. | |
| 2006/0042509 A1 | 3/2006 | Henglein et al. | |
| 2006/0047018 A1 | 3/2006 | Li et al. | |
| 2006/0225609 A1 | 10/2006 | Rueger et al. | |
| 2006/0254315 A1 | 11/2006 | Winkler et al. | |
| 2007/0104663 A1 | 5/2007 | Henglein et al. | |
| 2007/0199478 A1 | 8/2007 | Schlegl et al. | |
| 2007/0243149 A1 | 10/2007 | Hofacker et al. | |
| 2008/0181921 A1 | 7/2008 | DeLuca | |
| 2008/0274198 A1 | 11/2008 | Schweinfurth | |
| 2009/0252772 A1* | 10/2009 | Henglein ............ C09B 67/0098 424/401 | |
| 2009/0264575 A1 | 10/2009 | Henglein et al. | |
| 2010/0011992 A1* | 1/2010 | Bujard ................... B82Y 30/00 106/439 | |
| 2010/0047199 A1 | 2/2010 | Trummer et al. | |
| 2010/0095868 A1 | 4/2010 | Kaupp et al. | |
| 2010/0116169 A1 | 5/2010 | Kaupp et al. | |
| 2010/0175587 A1 | 7/2010 | Rueger et al. | |
| 2010/0297045 A1 | 11/2010 | Kaupp et al. | |
| 2010/0322981 A1 | 12/2010 | Bujard et al. | |
| 2011/0048276 A1 | 3/2011 | Schlegl et al. | |
| 2011/0160389 A1 | 6/2011 | Bubat et al. | |
| 2011/0226161 A1 | 9/2011 | Schumacher et al. | |
| 2011/0251293 A1 | 10/2011 | Trummer et al. | |
| 2011/0259243 A1 | 10/2011 | Schumacher et al. | |
| 2011/0265689 A1 | 11/2011 | Schumacher et al. | |
| 2011/0265690 A1 | 11/2011 | Schumacher et al. | |
| 2011/0306678 A1 | 12/2011 | Liu et al. | |
| 2013/0149363 A1 | 6/2013 | Schmidt et al. | |
| 2013/0164356 A1 | 6/2013 | Pfaff et al. | |
| 2013/0216597 A1 | 8/2013 | Mathias et al. | |
| 2014/0018439 A1 | 1/2014 | Gruner et al. | |
| 2014/0165878 A1 | 6/2014 | Chang et al. | |
| 2014/0251184 A1 | 9/2014 | McGuire et al. | |
| 2015/0259536 A1 | 9/2015 | Gruner et al. | |
| 2015/0344677 A1 | 12/2015 | Jones et al. | |
| 2016/0185972 A1 | 6/2016 | Schmidt | |

FOREIGN PATENT DOCUMENTS

| | | |
|---|---|---|
| CN | 1519278 A | 8/2004 |
| CN | 101289580 A | 10/2008 |
| CN | 102718229 A | 10/2012 |
| CN | 103183972 A | 7/2013 |
| CN | 104870571 A | 8/2015 |
| CN | 106536640 A | 3/2017 |
| DE | 1959998 A1 | 7/1971 |
| DE | 2522527 A | 12/1975 |
| DE | 19836810 A1 | 2/2000 |
| DE | 102010021530 A1 | 12/2011 |
| DE | 102011012214 A1 | 8/2012 |
| EP | 0289240 A1 | 11/1988 |
| EP | 0668329 A2 | 8/1995 |
| EP | 0708154 A2 | 4/1996 |
| EP | 0723997 A1 | 7/1996 |
| EP | 0753545 A2 | 1/1997 |
| EP | 0870730 A1 | 10/1998 |
| EP | 0950693 A1 | 10/1999 |
| EP | 1029900 A1 | 8/2000 |

(56) References Cited

FOREIGN PATENT DOCUMENTS

| | | | |
|---|---|---|---|
| EP | 1121334 A1 | 8/2001 | |
| EP | 1213330 A1 | 6/2002 | |
| EP | 1251152 A1 | 10/2002 | |
| EP | 1270682 A2 | 1/2003 | |
| EP | 1281732 A1 | 2/2003 | |
| EP | 1306412 A1 | 5/2003 | |
| EP | 0948572 B1 | 7/2003 | |
| EP | 1230310 B1 | 9/2003 | |
| EP | 1114103 B1 | 10/2003 | |
| EP | 1375601 A1 * | 1/2004 | ............... A61K 8/11 |
| EP | 1375601 A1 | 1/2004 | |
| EP | 1422268 A2 * | 5/2004 | ........... C09C 1/0015 |
| EP | 1422268 A2 | 5/2004 | |
| EP | 1230308 B1 | 8/2004 | |
| EP | 1474486 A2 | 11/2004 | |
| EP | 1546063 A1 | 6/2005 | |
| EP | 1553144 A1 | 7/2005 | |
| EP | 1572812 A1 | 9/2005 | |
| EP | 1621585 A2 | 2/2006 | |
| EP | 1685198 B1 | 5/2007 | |
| EP | 1980594 B1 | 6/2009 | |
| EP | 0948572 B2 | 1/2010 | |
| EP | 1829833 B1 | 1/2010 | |
| EP | 1699884 B1 | 2/2010 | |
| EP | 1025168 B2 | 8/2010 | |
| EP | 1587881 B1 | 12/2010 | |
| EP | 2217664 B1 | 6/2011 | |
| EP | 2371908 A2 | 10/2011 | |
| EP | 2508571 A1 | 10/2012 | |
| EP | 2042474 B1 | 3/2013 | |
| EP | 2576702 A1 | 4/2013 | |
| EP | 2346949 B1 | 7/2013 | |
| EP | 2346950 B1 | 7/2013 | |
| EP | 2356181 B1 | 7/2013 | |
| EP | 2367889 B1 | 7/2013 | |
| EP | 2698403 A1 | 2/2014 | |
| EP | 2318463 B1 | 10/2014 | |
| EP | 2632988 B1 | 10/2014 | |
| JP | 4949173 B | 12/1974 | |
| JP | 51143027 | 12/1976 | |
| JP | 5869258 A | 4/1983 | |
| JP | 6234962 A | 2/1987 | |
| JP | H5279594 A | 10/1993 | |
| JP | 711161 A | 1/1995 | |
| JP | 8259840 A | 10/1996 | |
| JP | H8302236 A | 11/1996 | |
| JP | 2005264144 A | 12/1997 | |
| JP | H10101377 A | 4/1998 | |
| JP | H11189734 A | 7/1999 | |
| JP | H11217516 A | 8/1999 | |
| JP | 2000081832 A | 3/2000 | |
| JP | 2001520296 A | 10/2001 | |
| JP | 2002509561 A | 3/2002 | |
| JP | 2002522618 A | 7/2002 | |
| JP | 2002537465 A | 11/2002 | |
| JP | 2005307155 A | 4/2005 | |
| JP | 2005515769 A | 6/2005 | |
| JP | 2005521754 A | 7/2005 | |
| JP | 2006160683 A | 6/2006 | |
| JP | 2008230997 A | 10/2008 | |
| JP | 2010507009 A | 3/2010 | |
| JP | 2011504193 A | 2/2011 | |
| JP | 2013520534 A | 6/2013 | |
| JP | 2013544919 A | 12/2013 | |
| JP | 2014527573 A | 10/2014 | |
| WO | 9638505 A1 | 12/1996 | |
| WO | 9746624 A1 | 12/1997 | |
| WO | 0021905 A1 | 4/2000 | |
| WO | 03006558 A2 | 1/2003 | |
| WO | WO-03006558 A2 * | 1/2003 | ............... C03C 3/06 |
| WO | 2004031102 A1 | 4/2004 | |
| WO | 2004055119 A1 | 7/2004 | |
| WO | 2004087816 A2 | 10/2004 | |
| WO | 2006021386 A1 | 3/2006 | |
| WO | 2006136435 A2 | 12/2006 | |
| WO | 2007115675 A2 | 10/2007 | |
| WO | 2008077612 A2 | 7/2008 | |
| WO | 2009144005 A1 | 12/2009 | |
| WO | 2011147892 A1 | 12/2011 | |
| WO | 2012130897 A1 | 10/2012 | |
| WO | 2014053454 A1 | 4/2014 | |
| WO | 2014094993 A1 | 6/2014 | |
| WO | 2015183674 | 12/2015 | |
| WO | 2015183674 A1 | 12/2015 | |

* cited by examiner

EFFECT PIGMENTS HAVING HIGH TRANSPARENCY, HIGH CHROMA AND HIGH BRILLIANCY, METHOD FOR THE PRODUCTION AND USE THEREOF

CROSS-REFERENCE TO RELATED APPLICATIONS

The present application is the national phase of PCT/EP2015/080859 filed Dec. 21, 2015 and claims priority to European Patent Application No. 14199293.3 filed Dec. 19, 2014, the entire disclosures of which are hereby incorporated by reference herein.

BACKGROUND OF THE INVENTION

Field of the Invention

The present invention relates to transparent effect pigments comprising a non-metallic platelet-shaped substrate and a coating applied thereto, wherein the coating comprises at least one spacer layer, a method for producing the transparent effect pigments as well as use thereof.

DESCRIPTION OF RELATED ART

Multilayer pigments which, based on a non-metallic platelet-shaped substrate, comprise at least one layer sequence of alternating high-, low-, high-refractive-index layers are known for example from EP 1 572 812 A1, EP 1 213 330 A1, EP 1 025 168 B2, EP 1 621 585 A2, EP 0 948 572 A1, EP 0 950 693 A1, EP 1 306 412 A1, EP 1 587 881 A2, EP 2 632 988 A1 or EP 1 474 486 A2. Depending on the optical layer thickness of the low-refractive-index layer, the multilayer pigments can exhibit a strong color change depending on the observation angle, as described e.g. in EP 1 375 601 A1, EP 1 281 732 A1, EP 0 753 545 A2 and US 2004/0003758 A1. All of the above-listed applications have in common the fact that a low-refractive-index layer, made of a low-refractive-index metal oxide, such as for example silicon oxide, is present in the layer sequence.

Compared with single-layer effect pigment with only a single identical first layer, multilayer pigments are characterized by a higher gloss and optionally by a higher chroma, here assuming of course the same substrate and same particle size.

EP 1 422 268 A2 discloses a pigment with a multilayer structure, wherein this pigment has two or more metal oxide layers, wherein the at least one metal (ion) of the metal oxide layer is selected from the group which consists of cerium, tin, titanium, iron, zinc and zirconium. This application relates to pigments with high chroma and high brilliance, which have the fewest possible and smallest possible pores in their coating. According to EP 1 422 268 A2 a small pore volume is to guarantee an optically high-quality coating.

US 2015/0344677 A1 relates to effect pigments based on coated platelet-shaped substrates. The coating comprises a first and a second high-refractive-index layer as well as a third component which is to diffuse partially or 100% into one or both of the high-refractive-index layers. The third component can be $SiO_2$ or another metal oxide. The aim of this application, in the case of effect pigments with a $D_{50}$ value of 15 μm or less, is to obtain an $SiO_2$ covering without agglomeration.

SUMMARY OF THE INVENTION

In some examples, there is provided a transparent effect pigment comprising a non-metallic platelet-shaped substrate and a coating applied to the substrate, wherein the coating comprises (a) optionally a layer 1 which comprises or consists of at least one of tin oxide, tin hydroxide or tin oxide hydrate, (b) a layer 2 comprising at least one of metal oxide, metal hydroxide or metal oxide hydrate, and (c) a layer 3 comprising at least one of metal oxide, metal hydroxide or metal oxide hydrate, and wherein at least one of layers 2 or 3 comprises at least two different metal ions and layers 2 and 3 are interrupted by a spacer layer. Also provided are methods for producing the transparent effect pigment.

Also provided are processes for producing a pigmented cosmetic formulation, plastic, film, textile, ceramic material, glass, paint, printing ink, ink, varnish, powder coating, coating composition or a material for a functional application comprising introducing the transparent effect pigment of the present invention into a cosmetic formulation, plastic, film, textile, ceramic material, glass, paint, printing ink, ink, varnish, powder coating, coating composition or a material for a functional application. Items comprising at least one transparent effect pigment of the present invention also are provided.

BRIEF DESCRIPTION OF THE DRAWINGS

The foregoing summary, as well as the following detailed description, will be better understood when read in conjunction with the appended drawings. In the drawings.

DETAILED DESCRIPTION

Figure 1:
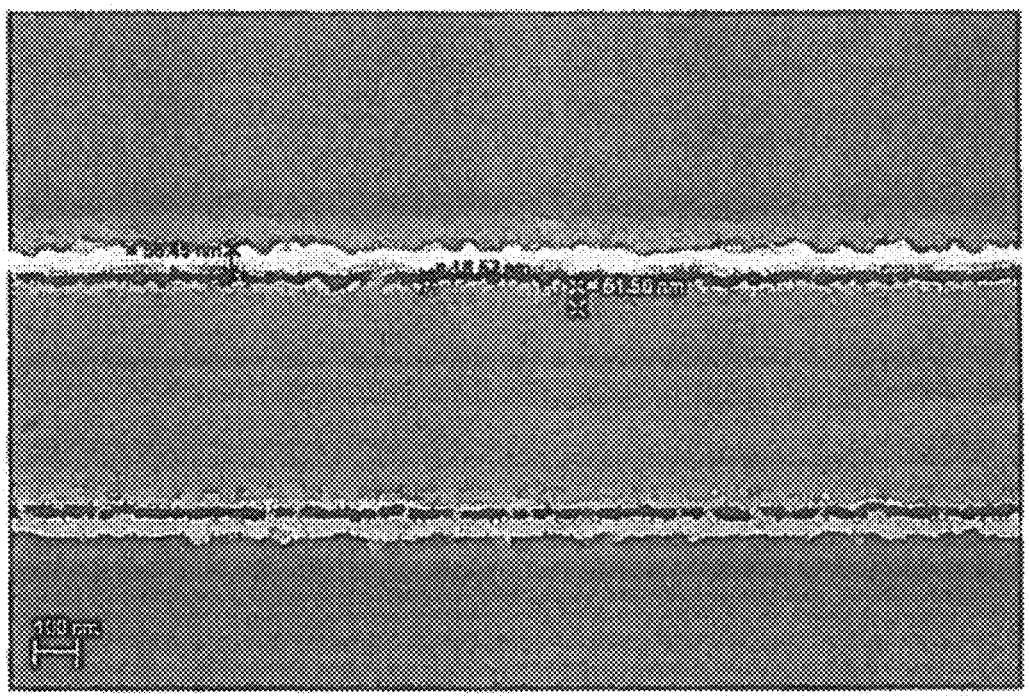
FIG. 1 is a scanning electron microscope polished cross-section photograph of an effect pigment according to the invention magnified 50,000 times (relative to Polaroid 545)
Figure 2:
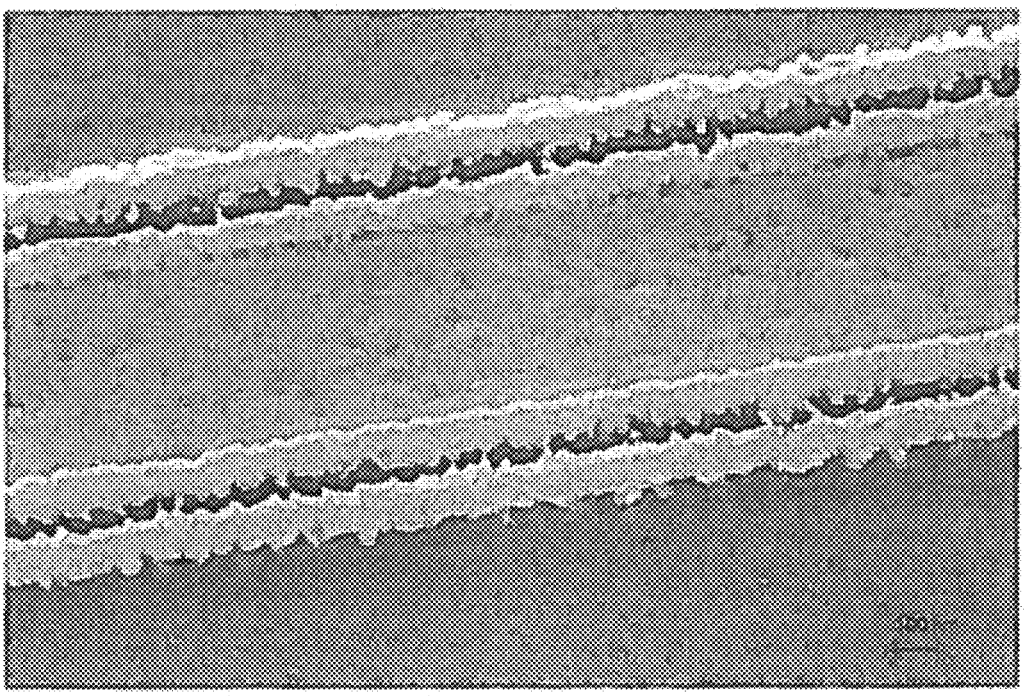
FIG. 2 is a scanning electron microscope polished cross-section photograph of an effect pigment according to the invention magnified 50,000 times (relative to Polaroid 545)
Figure 3:
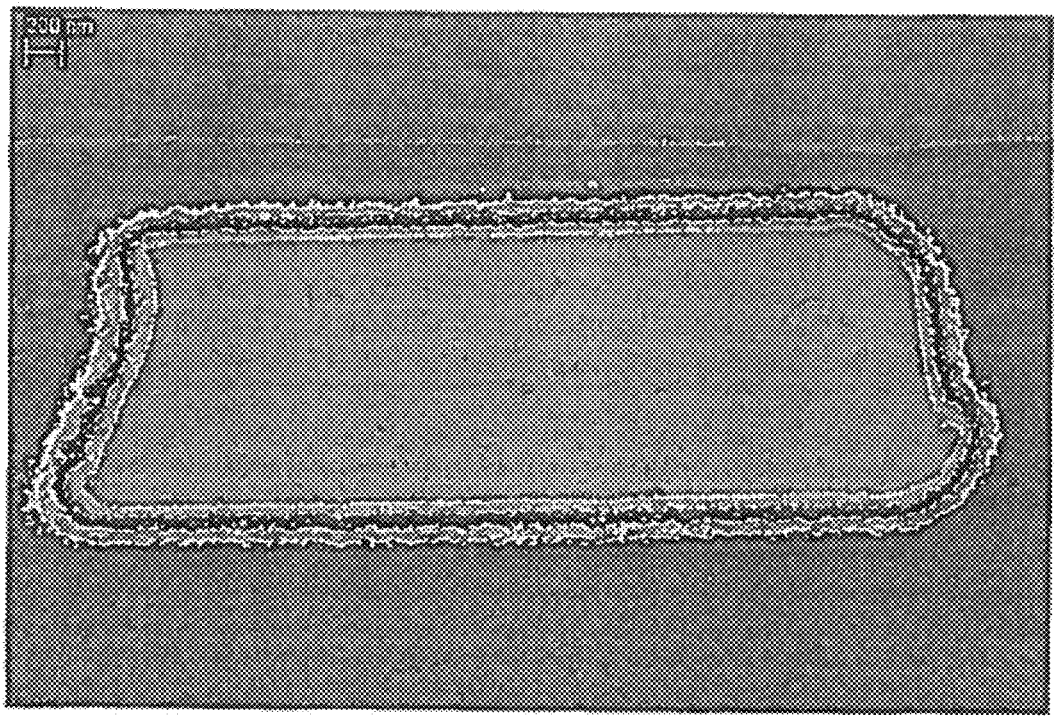
FIG. 3 is a scanning electron microscope polished cross-section photograph of an effect pigment according to the invention magnified 20,000 times (relative to Polaroid 545)

The object of the present invention is to provide a high-chroma pigment having high gloss which has no, or as little as possible, absorption color, a high mechanical stability as well as a high chemical stability and at the same time can be produced easily with low material usage.

This object is achieved by providing a transparent effect pigment which comprises a non-metallic platelet-shaped substrate and a coating applied to the substrate, wherein the coating has a) optionally a layer 1 which comprises or consists of tin oxide, tin hydroxide and/or tin oxide hydrate, b) a layer 2 comprising at least one metal oxide, metal hydroxide and/or metal oxide hydrate, c) a layer 3 comprising at least one metal oxide, metal hydroxide and/or metal oxide hydrate, and wherein at least one of layers 2 or 3 contains at least two different metal ions and layers 2 and 3 are interrupted by a spacer layer.

By "interrupted" is meant, according to the invention, that layers 2 and 3 are spaced apart from each other or held at a distance by the spacer layer.

By the general expression "metal oxide, metal hydroxide and/or metal oxide hydrate" is meant, according to the invention, "metal oxide and/or metal hydroxide and/or metal oxide hydrate". This also applies when the metal or metal ion is specified, for example as titanium (ion), iron (ion), tin (ion), zirconium (ion) etc.

By the expression "a metal ion" is meant, according to the invention, not an individual metal ion, but a plurality of metal ions.

According to a preferred variant, the optional layer 1 lies directly on the non-metallic platelet-shaped substrate, layer 2 follows layer 1 directly and layer 3 follows layer 2, wherein layers 2 and 3 are interrupted by a spacer layer.

According to a further preferred variant, layer 2 lies directly on the non-metallic platelet-shaped substrate, and layer 3 follows layer 2, wherein layers 2 and 3 are interrupted by a spacer layer.

Preferred developments of the transparent effect pigment are given in the dependent claims 2 to 9.

In addition, the object is achieved by providing a method for producing the transparent effect pigment according to the invention, wherein the method comprises the following steps:
(i) optionally applying a non-calcined layer which comprises or consists of tin oxide, tin hydroxide and/or tin oxide hydrate to the non-metallic platelet-shaped substrate,
(ii) sequentially applying three non-calcined layers A, B and C, in each case made of or with at least one metal oxide, metal hydroxide and/or metal oxide hydrate, wherein layers A, B and C are arranged directly on each other and wherein the at least one metal oxide, metal hydroxide and/or metal oxide hydrate applied in layer B, with respect to the metal ion, is different from the metal ion(s) of the metal oxides, metal hydroxides and/or metal oxide hydrates of layer A and layer C,
(iii) calcining the product obtained in step (ii) at a temperature from a range of from 600° C. to 1000° C., obtaining the transparent effect pigment comprising at least one spacer layer.

Alternatively, the object is achieved by providing method for producing the transparent effect pigment according to the invention, wherein the method comprises the following steps:
(i) sequentially applying two non-calcined layers B and C, in each case made of or with at least one metal oxide, metal hydroxide and/or metal oxide hydrate, to a calcined single- or multi-coated non-metallic substrate, wherein layers B and C are arranged directly on each other and wherein the at least one metal oxide, metal hydroxide and/or metal oxide hydrate applied in layer B, with respect to the metal ion, is different from the metal ion(s) of the metal oxides, metal hydroxide and/or metal oxide hydrate of layer C and the layer which directly adjoins layer B in the direction of the substrate,
(ii) calcining the product obtained in step (i) at a temperature from a range of from 600° C. to 1000° C., obtaining the transparent effect pigment comprising at least one spacer layer.

A subject of the invention is furthermore the use of the transparent effect pigment according to the invention in cosmetic formulations, plastics, films, textiles, ceramic materials, glasses, paints, printing inks, varnishes, powder coatings, and/or in functional applications such as e.g. for laser marking, IR reflection, photocatalysis.

In addition, the object on which the invention is based is achieved by providing an item, wherein the item has at least one transparent effect pigment according to the invention.

The non-metallic platelet-shaped substrates to be coated according to the invention are preferably transparent, i.e. they are at least partially permeable to visible light. By "partially permeable" is meant according to the invention that the opacity quotient $D_q$, defined as $$D_q = \frac{L^{*25}_{black}}{L^{*25}_{white}},$$

is preferably <0.35, further preferably <0.28, particularly preferably <0.22 and quit particularly preferably <0.20. The opacity quotient is here determined on the basis of varnish applications to black-white opacity charts (Byko Chart 2853, Byk-Gardner) of a nitrocellulose varnish to which 10 wt.-% of the respective substrate has been added (Erco bronze mixed varnish 2615e colorless: Maeder Plastiklack AG) according to IIc "Opacity comparison". $L^{-25}_{black}$ and $L^{-25}_{white}$ respectively are the lightness values measured at a measurement angle of 25° on a black or white background of the black-white opacity charts, preferably with Byk-Gardner's BYK-mac multi-angle colorimeter.

The non-metallic platelet-shaped substrates can be selected from the group consisting of natural mica platelets, synthetic mica platelets, glass platelets, $SiO_2$ platelets, $Al_2O_3$ platelets, kaolin platelets, talc platelets and bismuth oxychloride platelets. According to the invention the transparent effect pigments can also be based on mixtures of the above-indicated non-metallic platelet-shaped substrates. The above-named non-metallic platelet-shaped substrates can also have one or more layers made of or with at least one high- and/or low-refractive-index metal oxide, metal hydroxide and/or metal oxide hydrate and be calcined. Thus, pearlescent pigments or interference pigments can thus also be used as substrates. According to a preferred embodiment, the substrates to be used according to the invention are uncoated, non-metallic, platelet-shaped, substantially transparent, preferably transparent, substrates.

Preferably, the non-metallic platelet-shaped substrates are selected from the group consisting of natural mica platelets, synthetic mica platelets, glass platelets, $SiO_2$ platelets, $Al_2O_3$ platelets and mixtures thereof. Particularly preferably, the non-metallic platelet-shaped substrates are selected from the group consisting of natural mica platelets, synthetic mica platelets, glass platelets and mixtures thereof. Synthetic mica platelets and/or glass platelets as well as mixtures there of are quite particularly preferred as non-metallic platelet-shaped substrates. In particular, glass platelets are preferred as non-metallic platelet-shaped substrate.

The glass platelets that can be used as substrate can, with regard to their composition, consist of silicate glass, such as soda-lime glass, lead crystal glass, E-glass, A-glass, C-glass, ECR-glass, Duran glass, window glass, laboratory glass, aluminosilicate glass or borosilicate glass. The glass platelets preferably have a composition corresponding to the teaching, in particular corresponding to the main claim, of EP 1 980 594 B1, particularly preferably corresponding to the teaching, in particular corresponding to the respective main claim, of EP 1 829 833 B1 or EP 2 042 474 B1. The production of the glass platelets that can be used as substrate is preferably effected according to the method described in EP 289 240 B1.

In a further embodiment, the glass platelets can be dyed in a targeted manner during their production by the addition of at least one inorganic dye. Suitable dyes re those which do not decompose at the respective melting temperature of the glass composition. The proportion of dye here preferably lies in a range of from 0.1 wt.-% to 20 wt.-% in total, particularly preferably in a range of from 0.2 wt.-% to 15 wt.-% in total, and quite particularly preferably in a range of from 0.5 wt.-% to 10 wt.-% in total, in each case relative to the total weight of the glass composition. Suitable dyes are in particular elemental noble metals such as Au, Pd or Pl, the cations or complex anions of the elements Cu, Cr, Mn, Fe, Ti and/or Co as well as mixtures of the dyes listed above.

In a further embodiment, the refractive index of the glass platelets that can be used as substrate lies in a range of from 1.45 to 1.80, preferably in a range of from 1.50 to 1.70.

In a further embodiment, the platelet-shaped substrates, in particular glass platelets can be encased in a layer which comprises or consists of silicon oxide, silicon hydroxide, silicon oxide hydrate. For example, when glass substrates are used, the above-named coating can protect the glass surface from chemical change, such as swelling, teaching out of glass constituents of dissolution in aggressive acid covering solutions.

The synthetic mica platelets that can be used as substrate can have a composition according to the main claim of CN 102718229 A or according to the main claim of US 2014/0251184 A1. They can furthermore be produced according to the details in EP 0 723 997 A1, page 3 to page 4.

The synthetic mica platelets that can be used as substrate are preferably fluorphlogopite of the formula $KMg_3AlSi_3O_{10}F_2$, $KMg_2½(Si_4O_{10})F_2$ or $NaMg_2½(Si_4O_{10})f_2$, in particular fluorphlogopite of the formula $KMg_3AlSi_3O_{10}F_2$, which according to X-ray fluorescence (XRF) analysis preferably comprises the components named in Table 1 as respective metal oxide in the ranges listed there.

TABLE 1

Preferred compositions of synthetic mica platelets according to XRF analysis.
Composition of synthetic mica platelets, values in wt.-%, in each case relative to the total weight of the synthetic mica platelets

| | |
|---|---|
| $SiO_2$ | 38 to 46 |
| $Al_2O_3$ | 10 to 14 |
| $K_2O$ | 9 to 13 |
| $Fe_2O_3$ | 0.01 to 0.25 |
| MgO | 26 to 34 |
| MnO | 0 to 0.05 |
| $Na_2O$ | 0 to 13 |

The average thickness of the non-metallic platelet-shaped substrates to be coated preferably lies in a range of from 50 nm to 5000 nm, particularly preferably in a range of from 60 nm to 3000 nm and quit particularly preferably in a range of from 70 nm to 2000 nm. By the "average thickness" is meant according to the invention, the arithmetic mean, unless otherwise indicated.

In an embodiment, the average thickness for glass platelets as non-metallic platelet-shaped substrate to be coated lies in a range of from 750 nm to 1500 nm, preferably in a range of from 850 nm to 1400 nm and particularly preferably in a range of from 900 nm to 1300 nm. Thinner platelet-shaped substrates lead to a smaller total thickness of the transparent effect pigments according to the invention. Thus, glass platelets the average thickness of which lies in a ranges of from 50 nm to 700 nm, further preferably in a range of from 101 nm to 800 nm, particularly preferably in a range of from 160 nm to 500 nm and quite particularly preferably in a range of from 200 nm to 400 nm, are also preferred as non-metallic platelet-shaped substrate.

In a further embodiment, the average thickness of the natural or synthetic mica platelets as non-metallic platelet-shaped substrate to be coated preferably lies in a range of from 80 nm to 1300 nm, further preferably in a range of from 90 nm to 1000 nm, particularly preferably in a range of from 99 nm to 800 nm and quite particularly preferably in a range of from 200 nm to 600 nm.

If non-metallic platelet-shaped substrates below an average thickness of 50 nm are coated with for example high-refractive-index metal oxidase, extremely brittle pigments are obtained, which can already break during incorporation into the respective application medium, which in turn causes a significant reduction the gloss.

Above an average substrate thickness of 5000 nm, the pigments can become too thick overall. This is accompanied by a poorer specific opacity, i.e. the covered surface per weight unit of transparent effect pigment according to the invention is lower. In addition, such thick pigments are oriented to a lesser extent plane-parallel to the background in the application medium. A poorer orientation in turn results in a reduced gloss. Effect pigments that are too thick overall can also be disadvantageous in an application with regard to the haptics.

In an embodiment the relative standard deviation of the thickness distribution of the non-metallic platelet-shaped substrates is 15% to 100%, preferably 17% to 70%, particularly preferably 19% to 61% and quite particularly preferably 21% to 41%. The relative standard deviation in [%] is the quotient of calculated standard deviation and average thickness.

The average thickness of the non-metallic platelet-shaped substrate is determined on the basis of a hardened varnish film, so which the transparent effect pigments according to the invention are aligned substantially plane-parallel to the background, according to the details below in Section IIk, "Determining the average thickness of the non-metallic platelet-shaped substrates, the average layer thickness of layers 2 and 3, the average layer thickness of the entire coating, the average height $h_a$ of the spacer layer as well as the average height $h_H$ of the cavities". For this, a polished cross-section of the hardened varnish film is examined under a scanning electron microscope (SEM), wherein the thickness of the non-metallic platelet-shaped transparent substrate of at least 100 effect pigments is determined and statistically averaged. By the term "average" is always meant according to the invention the arithmetic mean value, unless otherwise indicated.

The scanning electron microscope photographs were obtained using polished cross-sections of the transparent effect pigments according to the invention, with a Supra 35 scanning electron microscope (Zeiss).

The transparent effect pigments according to the invention optionally comprise a layer 1 which comprises or consists of tin oxide, tin hydroxide and/or tin oxide hydrate. Layer 1 can optionally be present at least partially as a mixed layer with a layer directly adjoining layer 1, for example layer 2.

Layers 2 and 3 of the transparent effect pigments according to the invention, after calcining, are preferably high-refractive-index layers or respectively a high-refractive-index layer the refractive index of which is preferably n>1.8, particularly preferably n≥1.9 and quite particularly preferably n≥2.1. The selection of the at least two different metal ions in layers 2 and/or 3 is effected according to the invention such that the metal oxide(s), metal hydroxide(s) and/or metal oxide hydrate(s) being formed therefrom in layers 2 or 3 in each case preferably has or have an average refractive index of n>1.8.

The at least one metal oxide, metal hydroxide and/or metal oxide hydrate of layers 2 or 3 comprises at least two different metal ions, preferably selected from the group of metals consisting of Ti, Fe, Sn, Mn, Zr, Ca, Sr, Ba, Ni, Sb, Ag, Zn, Cu, Ce, Cr and Co, further preferably selected from the group of metals consisting of Ti, Fe, Sn, Mn, Zr, Ag, Zn, Cu and Ce, particularly preferably selected from the group of metals consisting of Ti, Fe, Sn, Ag, Zr and Ce, and quite particularly preferably selected from the group of metals consisting of Ti, Fe and Sn. According to the invention, the selection of the at least two different metal ions is effected here such that the resulting effect pigments according to the invention are transparent. By "transparent effect pigments" is meant in the context of this invention that their opacity quotient $D_q$, defined as $$D_q = \frac{L^{*25}_{black}}{L^{*25}_{white}},$$

is ≤0.55, preferably ≤0.50, particularly preferably ≤0.45 and quite particularly preferably ≤0.41. The opacity quotient is here determined on the basis of varnish applications to black-white opacity charts (Byko Chart 2853, Byk-Gardner) of a nitrocellulose varnish to which 6 wt.-% of the respective effect pigment according to the invention has been added (Erco bronze mixed varnish 2615e colorless; Maeder Plastiklack AG) according to the details below in Section IIc "Opacity comparison". the proportion of non-coloring metal ions selected from the group of metals consisting of Ti, Sn, Zr, Ca, Sr, Ba and Zn preferably >13 wt.-% in total, the proportion of non-coloring metal ions particularly preferably lies in a range of from 14 wt.-% to 80 wt.-% and quite particularly preferably in a range of from 21% to 65 wt.-%, and the proportion of coloring metal ions selected from the group of metals consisting of Fe, Ti, Sn, Mn, Ni, Sb, Ag, Cu, Ce, Cr and Co is preferably ≤4 wt.-% in total, the proportion of coloring metal ions particularly preferably lies in a range of from 0.5 wt.-% to 2.7 wt.-% and quite particularly preferably in a range of from 0.6 wt.-% to 2.1 wt.-%, in each case determined by means of XRF analysis, in each case calculated as elemental metal and in each case relative to the total weight of the transparent effect pigment according to the invention. The weight ratio of non-coloring metal ions to coloring metal ions n the transparent effect pigment according to the invention her is preferably >6, particularly preferably >8 and quite particularly preferably >10.

Coloring metal ions from the group of metals Ti and Sn relate in particular to Ti of oxidation state +3 or +2 and Sn of oxidation state +2.

The at least two different metal ions are preferably either present homogeneously distributed in layers 2 and/or 3 or form a gradient herein. In exceptional cases the at least two different metal ions can also be present inhomogeneously distributed in layers 2 and/or 3.

By "at least two different metal ions" is meant according to the invention that at least two metal ions of different elements are present, for example titanium and iron ions, or titanium and tin ions, or titanium and zirconium ins, or iron and tin ions, or iron and zirconium ions etc. The different metal ions can be present in a mixture of metal oxide and/or metal hydroxides and/or metal oxide hydrates and/or also in mixed oxides and/or mixed hydroxides and/or mixed oxide hydrates in layer 2 and/or layer 3 of the transparent effect pigment according to the invention. Layer 2 and/or layer 3 can comprise or consist of this mixture of metal oxides and/or metal hydroxides and/or metal oxide hydrates and/or mixed hydroxides and/or mixed oxide hydrates.

According to the invention, when the metal ions of Ti and Fe are used in layer 2 and/or in layer 3 in the calcined effect pigment according to the invention, the iron-ion-containing proportion of the respective layer is preferably present as iron titanate, preferably as pseudobrookite and/or pseudorutile.

In an embodiment, one of the two layers 2 or 3 comprises only one kind of metal ion, preferably selected from the group of metals consisting of Ti, Sn, Zr and Zn, further preferably consisting of Ti, Sn and Zr. Correspondingly, the respective other of the two layers 3 or 2 has at least two different metal ions, preferably selected from the group of metals consisting of Ti, Sn, Zr and Zn, further preferably consisting of Ti, Sn and Zr.

In a preferred embodiment, both layer 2 and layer 3 comprise at least one metal oxide, metal hydroxide and/or metal oxide hydrate, wherein the metal ions of the at least one metal oxide, metal hydroxide and/or metal oxide hydrate comprise or are at least two different metal ions, preferably selected from the group of metals consisting of Ti, Sn, Zr and Zn, further preferably consisting of Ti, Sn and Zr.

In a further embodiment, the layers 2 and 3 interrupted by the spacer layer are identical with respect to the respective composition.

If the transparent effect pigment according to the invention comprise at least one coloring metal ion selected from the group of metals consisting of Fe, Ti, Sn, Mn, Cu, Cr, Co, Ag and Ce, the proportion thereof, in each case determined by means of XRF analysis and in each case calculated as elemental metal, is preferably ≤4 wt.-% in total, further preferably in a range of from 0.1 wt.-% to 3.4 wt.-% in total, particularly preferably in a range of from 0.2 wt.-% to 3.7 wt.-% in total and quite particularly preferably in a range of from 0.3 wt.-% to 2.8 wt.-% in total, in each case relative to the total weight of the transparent effect pigment.

In a preferred embodiment, at least one of layers 2 or 3 comprises at least two different metal ions selected from the group of metals consisting of Ti, Fe, Sn, Mn, Zr, Ca, Sr, Ba, Ni, Sb, Ag, Zn, Cu, Ce, Cr and Co, wherein at least one of these two metal ions is selected from the group of metals consisting of Ti, Sn, Zr and Zn and wherein the proportion of coloring metal ions selected from the group of metals consisting of Fe, Ti, Sn, Mn, Cu, Cr, Co, Ag and Ce, in each case determined by means of XRF analysis and in each case calculated as elemental metal, is preferably ≤4 wt.-% in total, relative to the total weight of the transparent effect pigment according to the invention.

In a particularly preferred embodiment, at least one of layers 2 or 3 comprise metal oxides, metal hydroxides and/or metal oxide hydrates, wherein the metal ions of the metal oxides, metal hydroxides and/or metal oxide hydrates comprise or are the metals Ti and Fe, wherein the weight ratio of Ti to Fe, in each case determined by means of XRF analysis and in each case calculated as elemental metal, is preferably >6, further preferably >12, particularly preferably >48 and quite particularly preferably >96, and wherein the proportion of Fe, determined by means of XRF analysis and calculated as elemental metal, is preferably ≤4 wt.-%, relative to the total weight of the transparent effect pigment according to the invention.

In a further particularly preferred embodiment, at least one of layers 2 or 3 composes metal oxides, metal hydroxides and/or metal oxide hydrates, wherein the metal ions of the metal oxides, metal hydroxides and/or metal oxide hydrates comprise or are the metals Ti and Sn, wherein the weight ratio of Ti to Sn, each case determined by means of XRF analysis and in each case calculated as elemental metal, is preferably >2, further preferably >4, particularly preferably >5 and quite particularly preferably >6, and wherein the proportion of Sn, determined by means of XRF analysis and calculate as elemental metal, is preferably selected from a range of from 1 wt.-% to 25 wt.-%, further preferably from a range of from 2 wt.-% to 19 wt.-%, further preferably from a range of from 4 wt.-% to 17 wt.-%, further preferably from a range of from 7 wt.-% to 14 wt.-%, particularly preferably from a range of from 10 wt.-% to 19 wt.-% and quite particularly preferably from a range of from 2 wt.-% to 5 wt.-%, in each case relative to the total weight of the transparent effect pigment according to the invention.

In a further particularly preferred embodiment, at least one of layers 2 or 3 comprises metal oxides, metal hydroxides and/or metal oxide hydrates, wherein the metal ions of the metal oxides, metal hydroxides and/or metal oxide hydrates are the metals Ti and Zr, wherein the weight ratio of Ti to Zr, in each case determined by means of XRF analysis and in each case calculated as elemental metal, is preferably >2, further preferably >4, particularly preferably >5 and quite particularly preferably >6, and wherein the proportion of Zr, determined by means of XRF analysis and calculated as elemental metal, is preferably selected from a range of from 1 wt.-% to 25%, further preferably from a range of from 2 wt.-% to 19 wt.-%, particularly preferably from a range of from 4 wt.-% to 15 wt.-%, and quite particularly preferably from a range of 6 wt.-% to 14 wt.-%, in each case relative to the total weight of the transparent effect pigment according to the invention.

The metal oxide, metal hydroxide and/or metal oxide hydrate contents of the transparent effect pigments according to the invention are determined as respective metal oxide by means of X-ray florescence (XRF) analysis and can be calculated as respective elemental metal. For this, the transparent effect pigment is incorporated into a lithium tetraaborate glass tablet, fixed in solid sample measuring beakers and measured therefrom. The Thermo Scientific Advantix ARL device was used as measuring device.

The average layer thickness of layer 1 is preferably lass than 10 nm, particularly preferably less than 5 nm and quite particularly preferably less than 3 nm, wherein layer 1 completely encases or incompletely encases the non-metallic platelet-shaped substrate or an optionally present coating. The average layer thickness of layers 2 and 3 of the transparent effect pigments according to the invention in each case preferably lies in a range of from 30 nm to 300 nm, further preferably in each case in a range of from 35 nm to 250 nm, particularly preferably in each case in a range of from 40 nm to 230 nm and quite particularly preferably in each case in a range of from 50 nm to 180 nm.

In a preferred embodiment the average layer thicknesses of layers 2 and 3 are almost identical.

By "almost identical average layer thicknesses" is meant according to the invention that the quotient of the average layer thickness of layer 2 and the average layer thickness of layer 3 preferably lies in range of from 0.5 to 1.8, further preferably in a range of from 0.7 to 1.6, particularly preferably in a range of from 0.8 to 1.4 and quite particularly preferably in a range of from 0.9 to 1.2.

In a further embodiment, in the case of a composition of layers 2 and 3 differing in terms of material, the respective optical layer thickness thereof is approximately identical, wherein the optical layer thickness of layers 2 and 3 may or may not follow the known Lambda/4 role. The optical layer thickness is defined as the product of refractive index and average layer thickness of the respective layer.

The average layer thickness of the entire coating of the transparent effect pigments according to the invention is preferably ≤750 nm. The average layer thickness of the entire coating preferably lies in a range of from 50 nm to 550 nm, particularly preferably in a range of from 78 nm to 430 nm and quite particularly preferably in a range of from 95 nm to 340 nm.

By "entire coating" is meant the complete coating which, starting from the substrate surface, extends therefrom perpendicularly in one direction.

In an embodiment, the relative standard deviation of the layer thickness distribution of layers 2 and 3 is in each case 2% to 74%, preferably in each case 3% to 63%, particularly preferably in each case 4% to 57% and quite particularly preferably in each case 4% to 49% and the relative standard deviation of the layer thickness distribution of the entire coating is 0.3% to 31%, preferably 1% to 27%, particularly preferably 1.2% to 24% and quite particularly preferably 1.9% to 22%. The relative standard deviation in [%] is the quotient of associated standard deviation and average thickness.

The spacer layer between layers 2 and 3 is preferably arranged substantially parallel to the surface of the non-metallic platelet-shaped substrate. By "substantially parallel" is meant in the context of this invention that in a scanning electron microscope polished cross-section photograph a regression line placed through a spacer layer, with respect to a regression line placed on the surface of the non-metallic platelet-shaped, has a gradient preferably close to zero.

Figure 7:
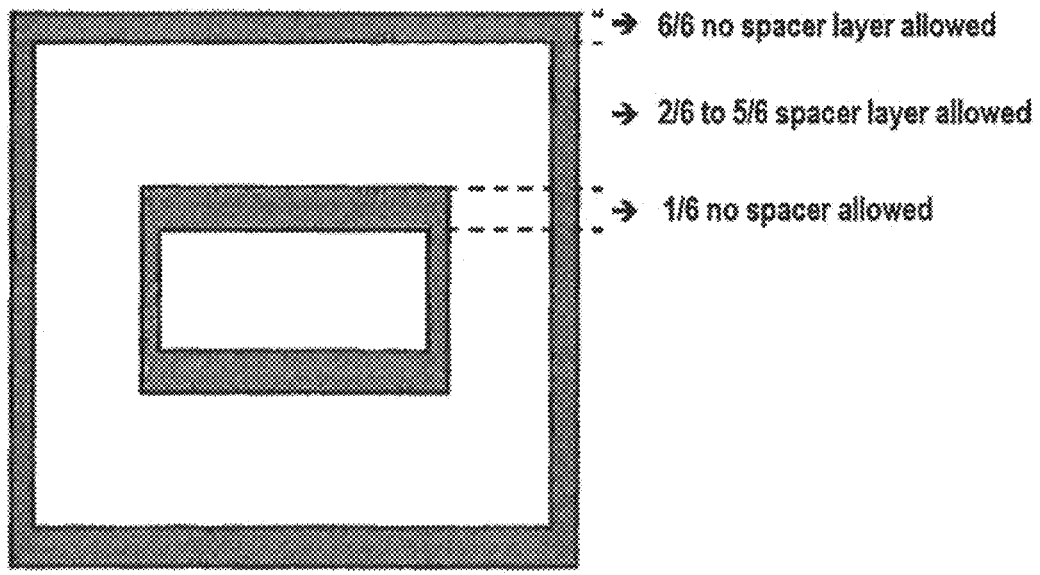
FIG. 7 is a schematic representation of the position of the spacer layer.

The position of the spacer layer within the entire coating can vary. If, for example, the average layer thicknesses of layers 2 and 3 are almost identical, the spacer layer, with respect to the entire coating, then lies approximately in the middle of the entire coating, preferably made of optional layer 1 as well as layers 2 and 3, as optional layer 1 is preferably extremely thin, particularly preferably only a few atomic layers thick. The spacer layer, with respect to the entire coating, preferably made of optional layer 1 as well as layers 2 and 3, is preferably arranged between the first sixth and the sixth sixth of the entire coating. The "first sixth" hare denotes proportion facing the non-metallic platelet-shaped substrate and the "sixth sixth" denotes the proportion, facing away from the non-metallic platelet-shaped substrate, of the entire coating, preferably made of optional layer 1 as well as layers 2 and 3 (FIG. 7).

The spacer layer formed between layers 2 and 3 preferably has connections which can also be called spacers which, on the one hand, connect the layers adjoining the spacer layer on both sides to each other and, on the other hand, keep them spaced apart from each other. As can be seen from polishes cross-section photographs taken using scanning electron microscopy, these connections or spacers can be arranged e.g. in the form of bars, which can also be called columns, at an angle of approximately 90°, for example from 80° is 100°, to the surface of the non-metallic platelet-shaped substrate. However, they can also form any other angle between 5° and 175°. The spacers. In particular bars, preferably the longitudinal axes of the spacers, preferably bars, are preferably arranged at an angle from a range of from 15° to 150° and particularly preferably at an angle from a range of from 35° to 135°, in each case to the surface of the non-metallic platelet-shaped substrate. When determining the angle, the substrate plane forms the first arm. One of the outsides of the bar observed in each case forms the second arm. Starting from the angle vertex of the two arms, the enclosed angle is determined, wherein, in the top view of the polished cross-section photographs taken using scanning electron microscopy, it is assumed to lie 0° to the left and 180° to the right in the substrate plane.

The connections or spacers can assume different geometric shapes and are preferably uniformly distributed over the entire spacer layer. For example, the connections or spacers can be present meshed, latticed, ladder-like, sponge-like or honeycombed. In some instances it is also possible to recognize structural elements which are similar to those in a photonic or inverse photonic crystal, such as for example known from EP 2 371 908 A2, EP 1 546 063 A1 or EP 1 121 334 A1.

The connections or spacers comprise at least one metal oxide, metal hydroxide and/or metal oxide hydrate. In a preferred embodiment the connections or spacers comprise a composition identical in terms of material to the layers located on both sides of the spacer layer. Alternatively, within the connections or spacers a gradient can also be formed between different metal oxides, metal hydroxides and/or metal oxide hydrates.

In a preferred embodiment, the connections or spacers comprise a metal oxide, metal hydroxide and/or metal oxide hydrate, wherein the metal ions of the metal oxides, metal hydroxides and/or metal oxide hydrates comprise or are at least two metal ions selected from the group of metals consisting of Ti, Fe, Sn, Mn, Zr, Ca, Sr, Ba, Ni, Ag, Zn, Cu, Ce, Cr and Co, further preferably from the group consisting of Ti, Fe, Sn, Mn, Zr, Ag, Zn, Cu and Co, particularly preferably from the group consisting of Ti, Fe, Sn, Zr, Ag and Ce, and quite particularly preferably from the group consisting of Ti, Fe and Sn.

The inventors assume that the connections or spacers can also effect a mechanical stabilization of the adjoining layers and thus of the transparent effect pigment according to the invention. A mechanically very stable effect pigment is presumably formed because of the number of connections or spacers, the different types of angle and geometric shapes which the connections or spacers can assume within the spacer layer, and the preferably uniform, two-dimensional distribution thereof within the spacer layer. The adhesion between the entire coating, preferably made of optional layer 1 as well as layers 2 and 3, and the non-metallic platelet-shaped substrate is very good in the case of the transparent effect pigments according to the inversion. The transparent effect pigments according to the invention even survive extreme shear conditions such as occur in the so-called Waring Blender Test without detectable damage. The performance of the Waring Blender Test is described below in Section IIf "Waring Blender Test".

In addition to their surprisingly good mechanical stability, the transparent effect pigments according to the invention have excellent chemical resistance, as will be explained according to the statements below in Section IIg "Determination of the chemical resistance".

Figure 6:
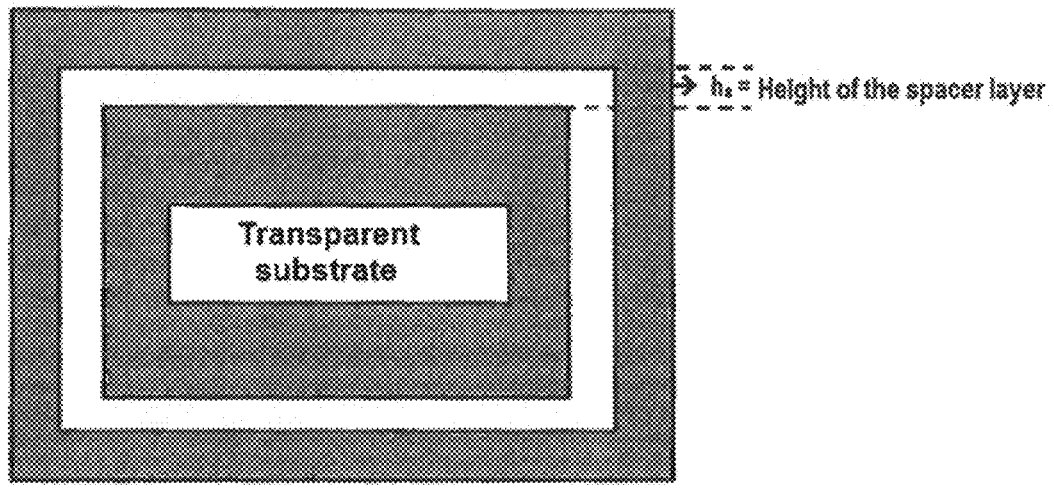
FIG. 6 is a schematic representation of the spacer layer.

The spacer layer of the transparent effect pigments according to the invention preferably has an average height $h_a$ from a range of from 5 nm to 120 nm, further preferably from a range of from 10 nm to 105 nm, further preferably from a range of from 16 nm to 90 nm, further preferably from a range of from 21 nm to 76 nm, particularly preferably from a range of from 22 nm to 67 nm and quite particularly preferably from a range of from 26 nm to 60 nm (FIG. 6).

To determine the average height $h_a$ of the spacer layer, the respective average layer thickness of layers 2 and 3 as well as the average layer thickness of the entire coating, on the basis of scanning electron microscope polishes cross-section photographs, the upper and lower substrate surface is respectively used as base line. By "upper and lower substrate surface" is meant in each case the longer side of the non-metallic platelet-shaped substrate in the scanning electron microscope polished cross-section photograph. The base tine is placed in the scanning electron microscope polished cross-section photograph, along the surface of the non-metallic platelet-shaped substrate, by connecting the two intersections, substrate—optional layer 1 or substrate—layer 2, with each by a straight line from the left- and right-hand edge of the scanning electron microscope polished cross-section photograph.

Figure 4:
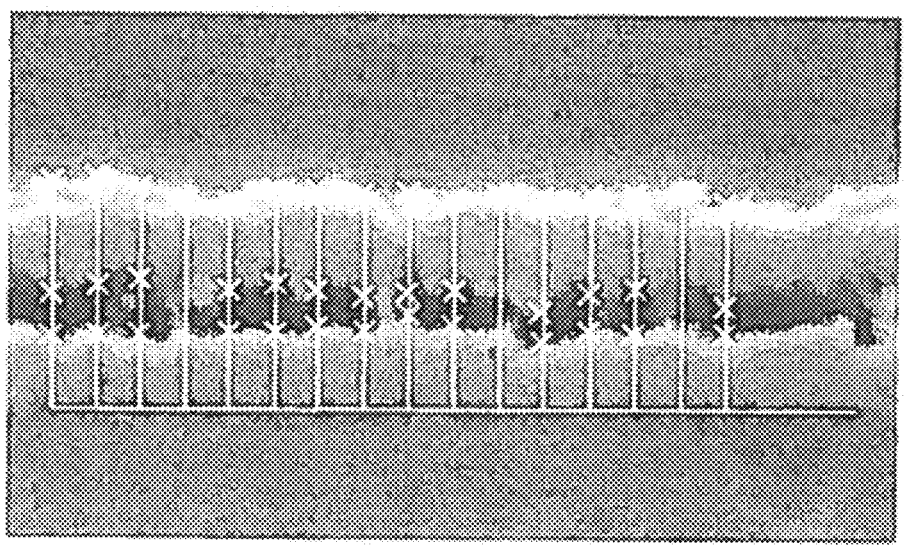
FIG. 4 is a section of the scanning electron microscope polished cross-section photograph from FIG. 2 with base line drawn in at the non-metallic platelet-shaped substrate-coating boundary surface and lines arranged vertical to the base line. The intersections at the boundary surfaces are marked with an "x"

The scanning electron microscope polished cross-section photographs were examined using AxioVision 4.6.3. Image-processing software (Zeiss). At an angle of 90° to the upper and lower base lines, which correspond to the two surfaces of the platelet-shaped substrate, so many parallel lines are drawn in 50 nm apart that a grid is placed over the effect pigment shown in the scanning electron microscope polished cross-section photograph (FIG. 4). The magnification of the scanning electron microscope polished cross-section photograph is preferably at least 50,000 times, relative to Polaroid 545 (4"×5"). Starting from the respective base line of the non-metallic platelet-shaped substrate. In the direction of the external layer 3 in each case or the outermost layer in each case, the intersections between the parallel lines arranged perpendicular to the respective base line and the respective boundary surfaces, of optional layer 1 to layer 2, of layer 2 to the spacer layer, of the spacer layer to layer 3 and of layer 3 to the environment or to a possible further applied layer are measured manually. It can occur here that one of the lines drawn in 50 nm apart comes to lie directly over a connection point or a spacer. In this case only the respective intersection of the fine at the boundary surface of layer 3 to the environment or to a possible further applied layer is recorded.

From these measured values, the layer thicknesses of layers 2 and 3, the layer thickness of the entire coating, the layer thickness of optionally further present layers as well as the height $h_a$ of the spacer layer are obtained by subtraction. The layer thickness of layer 2 is obtained from the difference between the respective measured intersections at the respective boundary surfaces of layer 2 to the spacer layer and either optional layer 1 to layer 2 or the base line to layer 2, provided that the non-metallic platelet-shaped substrate is not previously covered with further layers. The layer thickness of layer 3 is obtained from the difference between the respective measured intersections of layer 3 to the environment or a possible further applied coating and the spacer layer to layer 3. The layer thickness of the entire coating is obtained from the difference between the respective intersections of layer 3 to the environment or a possible further applied coating to the environment and the respective base line. The height $h_a$ of the spacer layer is obtained from the difference between the respective measured intersections of the spacer layer to layer 3 and layer 2 to the spacer layer. The layer thicknesses of possible further applied layers are to be determined analogously and to be taken into consideration correspondingly during the subtraction.

From the individual values of the layer thicknesses or of the height $h_a$ determined in this way, the respective arithmetic mean values are formed, in order to determine the above-indicated values of the average layer thicknesses or of the average height $h_a$. For meaningful statistics, the measurements described above are carried out on at least 100 of the parallel lines arranged perpendicular to the base line.

Furthermore, using the lines described above, which are drawn 50 nm apart into a scanning electron microscope photograph, the number of connections or spacers per micrometer as well as the bar number density, defined as the number of connections or spacers per number of lines as a percentage, is determined.

The height $h_{ms}$ denotes the middle of the spacer layer. It results as the sum of the layer thickness of optional layer 1, layer 2 and half of the height $h_a$ of the spacer layer. The relative height $h_{Rms}$ of the middle of the spacer layer is formed from the ratio of $h_{ms}$ and the layer thickness of the entire coating. The standard deviation of the relative height $\sigma h_{Rms}$ preferably lies in a range of from 0.2% to 18%, further preferably in a range of from 0.3% to 15%, particularly preferably in a range of from 0.4% to 11% and quite particularly preferably in a range of from 0.5% to 8%. The standard deviation of the relative height $\sigma h_{Rms}$ is a measure of the fact the spacer layer is arranged in a defined position parallel to the surface of the non-metallic platelet-shaped substrate within the entire coating.

If the transparent effect pigments according to the invention have at least one further spacer layer, their heights $h_{ms}$ as well as the relative height of the middle of the at least one further spacer layer $h_{Rms}$ are also determined via the method described above on the basis of polished cross-section photographs taken using scanning electron microscopy. The above-indicated values for the standard deviation of the relative height $\sigma h_{Rms}$ apply correspondingly to further spacer layers.

Figure 5:
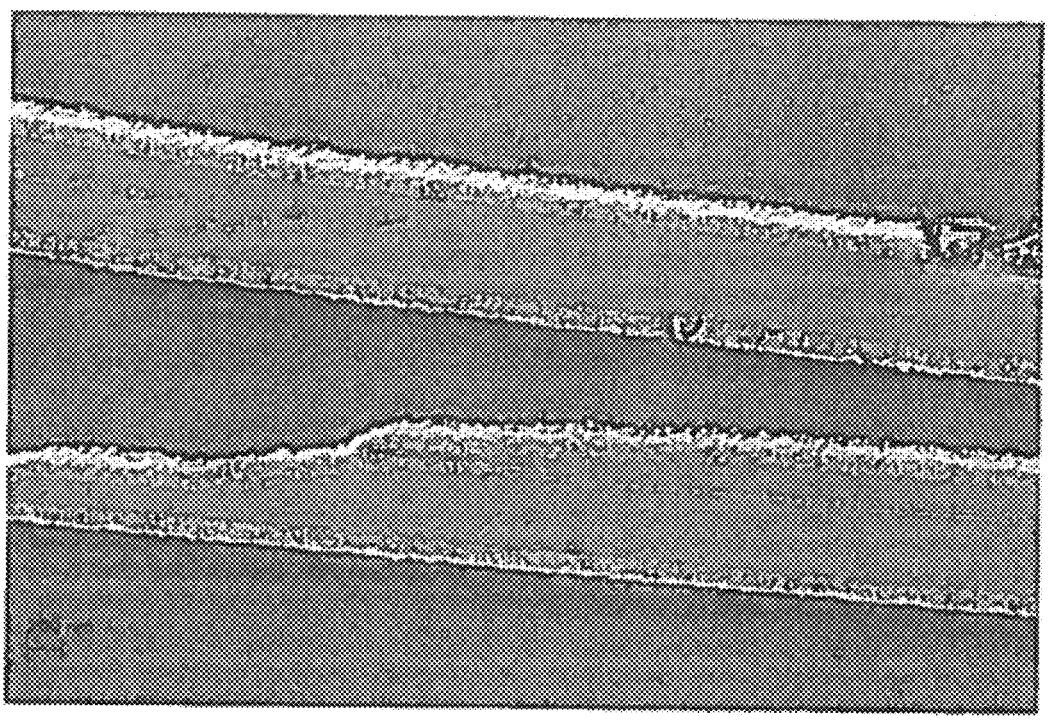
FIG. 5 is a scanning electron microscope polished cross-section photograph of comparison example 3 magnified 20,000 times (relative to Polaroid 545)

It is known to a person skilled in the art that for example pearlescent pigments coated with titanium dioxide have pores in the coating which are statistical distributed over the entire coating (FIG. 5). These pearlescent pigments do not have a spacer layer. The spacer layer, as well as the cavities of the transparent effect pigments according to the invention located within the spacer layer, however, are not statistically distributed over the entire coating, but arranged within the entire coating parallel to the surface of the non-metallic platelet-shaped substrate.

The distances from the centers of the statistically distributed pores to the substrate surface were also determined on the basis of scanning electron microscope polished cross-section photographs according to the method described above. For this, at an angle 90° to the upper lower base lines, which correspond to the two surfaces of the platelet-shaped substrate, so many parallel lines were drawn in 50 nm apart that a grid was placed over the pearlescent pigment without a spacer layer shown in the scanning electron microscope polished cross-section photograph. If one of the parallel lines came to lie over one or more pores, their height(s), their pore center(s) and the distance from the pore center or pore centers to the substrate surface was determined. A standard deviation can also be determined from the statistical distribution of the pore centers. In pearlescent pigments from the state of the art, i.e. in the case of pearlescent pigments without a spacer layer, the standard deviation of the distances from the centers of the statistically distributed pores to the substrate surface is >20%. The standard deviation of the distances from the centers of the statistically distributed pores to the substrate surface thus clearly differs in value from the standard deviation of the relative height of the center of the spacer layer of the transparent effect pigments according to the invention.

Thus the standard deviation of the distances from the pore centers to the substrate surface of pearlescent pigments without a spacer layer can be contrasted with the standard deviation of the relative height of the middle of the spacer layer of transparent effect pigments according to the invention.

If the transparent effect pigments according to the invention have more than one spacer layer within the coating, the method just described for measuring the individual layers and the spacer layers is correspondingly transferred.

In an embodiment, the relative standard deviation of the height distribution of the spacer layer is 4% to 75%, preferably 7% to 89%, particularly preferably 9% to 63% and quite particularly preferably 13% to 60%. The relative standard deviation in [%] of the height distribution is the quotient of the calculated standard deviation and the average height.

In a preferred embodiment, the transparent effect pigments according to the invention within the at least one spacer layer have a number of connections or spacers per micrometer from a range of from 0 to 17, further preferably from a range of from 0 to 14, particularly preferably from a range of from 1 to 11 and quite particularly preferably from a range of from 1 to 9.

In a preferred embodiment the transparent effect pigments according to the invention within the at least one spacer layer have a bar number density, defined as the number of connections or spacers per number of lines has as a percentage, of <85%, preferably from a range of from 1% to 75%, particularly preferably from a range of from 1% to 63% and quite particularly preferably from a range of from 1% to 49%.

Above a bar number density of 85%, within the meaning of this invention, a spacer layer is no longer discussed, as the high proportion of connections or spacers then leads to a virtually continuous coating.

In a further preferred embodiment, the transparent effect pigments according to the invention comprise at least one spacer layer arranged substantially parallel to the surface of the non-metallic platelet-shaped substrate, wherein the at least one spacer layer in each case has an average height $h_a$ from a range of from 19 nm to 83 nm, particularly preferably from a range of from 27 nm to 66 nm and quite particularly preferably from range of from 33 nm to 57 nm.

In a particularly preferred embodiment, the transparent effect pigments according to the invention have at least one spacer layer of average height $h_a$ from a range of from 16 nm to 79 nm, preferably from a range of from 21 nm to 66 nm and quite particularly preferably from a range of from 23 to 57 nm, wherein within the at least one spacer layer the number of connections or spacers per micrometer is selected from a range of from 0 to preferably from a range of from 0 to 6, particularly preferably from a range of from 1 to 5 and quite particularly preferably from a range of from 1 to 4.

In addition to the connections or spacers described above, the spacer layer comprises cavities. These cavities are spatially delimited by layers 2 and 3 as well as the connections or spacers.

Energy-dispersive X-ray microanalysis (EDX analysis) of these cavities does not give any indication of solid or liquid material, with the result that the inventors, using the analysis methods available at the present time, assume that the cavities within the spacer layer comprise a gas, presumably air. The connections or spacers, on the other hand, comprise at least one metal oxide, metal hydroxide and/or metal oxide hydrate, as stated above.

The cavities within the spacer layer of the transparent effect pigments according to the invention can adopt an average height $h_H$ from a range of from 2 nm to 119 nm, preferably from a range of from 6 nm to 105 nm, particularly preferably from a range of from 11 nm to 85 nm and quite particularly preferably from a range of from 18 nm to 53 nm. By the "height $h_H$" is meant the greatest distance between the bottom and top cavity boundary, it is determined according to the method described above for the height $h_a$, in which, in polished cross-section photographs taken using scanning electron microscopy, at an angle of 90° to the surface of the non-metallic platelet-shaped substrate, parallel lines are drawn in 50 nm apart. The difference between the two intersections of these lines with the upper and lower cavity boundary is represented by the height $h_H$. Here too, for meaningful statistics, the measurements described above are carried out on at least 100 lines.

The average height $h_a$ therefore represents a maximum value for the average height $h_H$. Accordingly, several cavities can also be present one above the other within the spacer layer.

The average height of the spacer layer $h_a$ as well as the average height of the cavities $h_H$ is determined on the basis of a hardened varnish film, in which the transparent effect pigments according to the invention are aligned substantially plane-parallel to the background, according to the statements in Section IIk "Determining the average thickness of the non-metallic platelet-shaped substrates, the average layer thickness of layers 2 and 3, the average layer thickness of the entire coating, the average height $h_a$ of the spacer layer as well as the storage height $h_H$ of the cavities". For this, a polished cross-section of the hardened varnish film is examined under a scanning electron microscope (SEM), as described above for $h_a$. Alternatively to those polished cross-sections, the transparent effect pigments according to the invention can be cut by means of the FIB (focused ion beam) method. For this, a fine beam of highly accelerated ions (e.g. gallium, xenon, neon or helium) is focused at a point by means of an ion-optical system and guided line by line over the effect pigment surface to be processed. The ions emit most of their energy on impact with the effect pigment surface and destroy the coating of this point, which leads to material removal line by line. Also, on the basis of the scanning electron microscope photographs than taken, the average height $h_a$, the average layer thickness of layers 2 and 3 as well as the average layer thickness of the entire coating can be determined according to the above-described method. Also, the average thickness of the non-metallic platelet-shaped substrate can be determined on the basis of scanning at electron microscope photographs of the effect pigments out by the FIB method.

In a further embodiment, the transparent effect pigments according to the invention within the spacer layer, distributed over the entire effect pigment, measured on the basis of scanning electron microscope polished cross-section photographs, comprise a surface properties of cavities from a range of from 51% to 99%, preferably from a range of from 63% to 96%, particularly preferably from a range of from 76% to 95% and quite particularly preferably from a range of from 84% to 94%. The connections or spacers preferably have a surface proportion from a range of from 1% to 49%, particularly from a range of from 4% to 37%, particularly preferably from a range of from 5% to 24% and quite particularly preferably from a range of from 6% to 16%.

Furthermore, it is preferable for the total volume occupied by the connections or spacers in spacer layer so be smaller than the total volume occupied by the cavities.

Preferably, the total volume occupied by the connections or spacers in the spacer layer is less than 50 vol.-%, further particularly less then 30 vol.-%, particularly preferably less then 20 vol.-% and quite particularly preferably less than 10 vol.-% of the total volume occupied by the cavities.

In the transparent effect pigments according to the invention, the cavities located within the spacer layer, unlike the pores of the teaching according to EP 1 422 268 A2, are expressly desired. According to EP 1 422 268 A2, a coating with low porosity and pores as small as possible is required in order to obtain pigments with high chroma and high brilliance. The pigments according to EP 1 422 268 A2 do not have a spacer layer. According to the invention, the cavities which are not distributed randomly within the entire coating, but located substantially parallel to the surface of the non-metallic platelet-shaped substrate within the spacer layer do not have a negative influence on the optical properties of the transparent effect pigments according to the invention. On the contrary, the transparent effect pigments according to the inversion are characterized, compared with pigments coated with a single layer, by a higher gloss as well as optionally a higher chroma, assuming of course the same non-metallic platelet-shaped substrate, the same particle size and identical first coating.

This higher gloss can be explained by the fact that the difference in refractive index between the spacer layer and the layers, adjoining it is maximal, which according to Fresnel's law in each case leads to maximum light reflection on these boundary surfaces. For the causes, the refractive index of air of approximately 1 is used as a basis here. A light beam impinging on the spacer layer is partially rejected on the boundary surfaces thereof, wherein the respective intensity of the reflection according to Fresnel's law is dependent on the difference in refractive index of the layers adjoining the spacer layer. As such a partial reflection takes place at each individual boundary surface, the total reflection also increases with the number of boundary surfaces. In the case of transparent effect pigments according to the invention, a light beam is thus partially reflected several times, which has the effect of a clearly stronger gloss and a stronger intensity of the interference color compared with conventional single-coated pigments.

If the cavities are statistically distributed within the entire coating, i.e. not substantially parallel to the non-metallic platelet-shaped substrate, the optical path length varies within the entire coating. This results in the interference conditions not being sufficiently met, and thus no strengthening or disappearance takes place.

The gloss of the transparent effect pigments according to the invention is determined on the basis of black-white opacity charts using a Byk-Gardner Micro-TRI-Gloss gloss meter, according to the statements below in Section IId "Gloss measurements". The chroma of the transparent effect pigments according to the invention is also determined on the basis of black-white opacity charts with the BYK-mac multi-angle colorimeter (Byk-Gardner) as explained below in Section IIb "Angle-dependent color measurements", further optical effects, such as glitter and granularity, are determined according to the statements below in Section IIe "Effect measurements".

In an embodiment, the transparent effect pigments according to the invention comprise, in addition to the above-described layers 1, 2 and 3, further high- and/or low-refractive-index layers which, observed from the nonmetallic platelet-shaped substrate, can be arranged either below optional layer 1 or layer 2 and/or above layer 3. These further layers can comprise metal oxides, metal hydroxides, metal oxide hydrates, wherein the metal ions of the metal oxides, metal hydroxides, metal oxide hydrates comprise or are at least one metal ion from the group of metals consisting of Ti, Fe, Sn, Mn, Zr, Ca, Sr, Ba, Ni, Ag, Zn, Cu, Ce, Cr and Co, preferably selected from the group of metals consisting of Ti, Fe, Sn, Zr, Ag, Zn, Cu, Ce, Cr and particularly preferably selected from the group of metals consisting of Ti, Fe and Sn. In addition, these further savers can comprise semitransparent metals selected from the group consisting of Ag, Al, Cr, Ni, Au, Pt, Pd, Cu, Zn and Ti, preferably selected from the group consisting of Ag, Au and Cu, or in each case alloys and/or mixtures thereof. According to the invention the further layers are selected such that the proportion of coloring metal ions selected from the group of metals consisting of Fe, Ti, Sn, Mn, Cu, Cr, Co, Ag and Ce, in each case determined by means of XRF analysis and is each case calculated as elemental metal, is preferably ≤4 wt.-% in total, further preferably in a range of from 0.1 wt.-% to 3.4 wt.-% in total, particularly preferably in a range of from 0.2 wt.-% to 3.7 wt.-% total and quite particularly preferably in a range of from 0.3 wt.-% to 2.8 wt.-% in total, in each case restive to the total weight of the transparent effect pigment. Furthermore, the proportion of at least one semitransparent metal, determined by means of XRF analysis, is preferably ≤2 wt.-% in total, particularly preferably in a range of from 0.03 wt.-% to 1.3 wt.-% in total and quite particularly preferably in a range of from 0.1 wt.-% to 0.8 wt.-%, in each case relative to the total weight of the transparent effect pigment. If the transparent effect pigments according to the invention comprise at least one coloring metal ion and at least one semitransparent metal, irrespective of whether in the non-metallic platelet-shaped substrate or in the coating, the proportion thereof preferably ≤4 wt.-% in total, relative to the total weight of the transparent effect pigment.

In an embodiment, each of the layers of the transparent effect pigments according to the invention can be provided with a doping, wherein the doping can comprise metal oxides, metal hydroxides and/or metal oxide hydrates, and the metal ions of the metal oxides, metal hydroxides and/or metal oxide hydrates comprise or are at least one metal ion selected from the group of metals consisting of Ca, Mg, Al, Ce, Zr or Sn, preferably Al, Zr or Sn. The proportion of doping is preferably ≤1 wt.-% in total, particularly preferably ≤0.5 wt.-% in total and quite particularly preferably ≤0.2 wt.-% in total, in each case relative to the total weight of the transparent effect pigments.

In a further embodiment, in addition to the spacer layer between layers 2 and 3, the entice coating of the transparent effect pigments according to the invention can comprise at least one further spacer layer which is also arranged substantially parallel to the surface of the non-metallic platelet-shaped substrate. The transparent effect pigments according to the invention preferably have no more than four spaces layers within the entire coating, as their optical quality then decreases. According to the invention, even if the transparent effect pigment according to the invention comprises more than one spacer layer, with respect to the entire coating, there is no spacer layer either in the first sixth or in the sixth sixth of the entire coating.

The transparent effect pigments according to the invention can thus have different interference colors depending on their coating.

The transparent effect pigments according to the invention can have any desired average particle size $D_{50}$. The $D_{50}$ values of the transparent effect pigments according to the invention preferably lie in a range of from 3 μm to 350 μm. The $D_{50}$ values of the transparent effect pigments according to the invention preferably lie in a range of from 4 μm to 211 μm, further preferably in a range of from 6 μm to 147 μm, particularly preferably in a range of from 7 μm to 99 μm and quite particularly preferably in a range of from 8 μm to 56 μm. Extremely preferably, the transparent effect pigments according to the invention have a $D_{50}$ value from a range of from 3 μm to 15 μm or from a range of from 10 μm to 35 μm or from a range at from 25 μm to 45 μm or from a range of from 30 μm to 65 μm or from a range of from 40 μm to 140 μm or from a range of from 135 μm to 250 μm.

The $D_{10}$ values of the transparent effect pigments according to the invention preferably comprise a range of from 1 μm to 120 μm. Particularly preferably, the $D_{10}$ values of the transparent effect pigments according to the invention lie in a range of from 1 μm to 5 μm or in a range of from 5 μm to 25 μm or in a range of from 10 μm to 30 μm or in a range of from 20 μm to 45 μm or in a range of from 25 μm to 65 μm or in a range of from 75 to 110 μm.

The $D_{90}$ values of the transparent effect pigments according to the invention preferably comprise a range of from 6 to 500 μm. Particularly preferably, the $D_{90}$ values of the transparent effect pigments according to the invention lie in a range of from 8 μm to 250 μm or in a range of from 10 μm to 150 μm or in a range of from 40 μm to 70 μm or in a range of from 68 μm to 110 μm or in a range of from 120 μm to 180 μm or in a range of from 400 μm to 490 μm.

The $D_{10}$, $D_{50}$ or $D_{90}$ value of the cumulative frequency distribution of the volume-averaged size-distribution function, as obtained by laser diffraction methods, indicates that 10%, 50% or 90% of the measured effect pigments have a volume-averaged diameter which is equal to or smaller then the value indicated in each case. The size-distribution curve of the transparent effect pigments according to the invention is here determined with Malvern's Mastersizer 2000 device according to the manufacturer's instructions. The evaluation of the scattered light signals is effective according to the Fraunhofer theory, which also includes refraction and absorption behaviors of the particles.

In a preferred embodiment, the transparent effect pigments according to the invention have a span ΔD, defined as $$\Delta D = \frac{D_{90} - D_{10}}{D_{50}},$$

from a range of from 0.7 to 2.0, preferably from a range of from 0.7 to 1.5, further preferably from a range of from 0.8 to 1.3, particularly preferably from a range of from 0.8 to 1.2 and quite particularly preferably from a range of from 0.85 to 1.1. The advantages of a narrow size classification with respect to color purity and/or gloss of the resulting effect pigments are described for example in EP 2 217 664 A1, EP 2 346 950 A1, EP 2 356 181 A1, EP 2 346 949 A1; EP 2 367 889 A1.

The transparent effect pigments according to the invention can be produced as follows:
  suspending the non-metallic platelet-shaped substrates in water at a temperature from a range of from 50° C. to 100° C.,
  optionally applying a non-calcined layer, which comprises or consists of tin oxide, tin hydroxide and/or tin oxide hydrate, by adding a water-soluble tin salt with simultaneous addition of a mineral base, sequentially applying three non-calcined layers A, B and C in the form of metal oxides, metal hydroxides and/or metal oxide hydrates by sequentially adding three water-soluble metal salts, in each case with simultaneous addition of mineral base, therein the second water-soluble metal salt—for producing layer B—with respect to the metal ion is different from the other two water-soluble metal salts for producing layer A or layer C, separating the coated substrates from the coating solution(s), optionally washing and/or optionally drying the coated substrates, calcining the coated substrates at temperatures from a range of from 600° C. to 1100° C., preferably from a range of from 625° C. to 930° C. and particularly preferably from a range of from 750° C. to 890° C., obtaining the transparent effect pigments according to the invention comprising at least one spacer layer.

In a preferred embodiment, the transparent effect pigments according to the invention are produced according to the above method.

The application, preferably deposition, of the respective moist oxides, metal hydroxides and/or metal oxide hydrates is preferably effected at a constant pH in a range of from pH 1.4 to 10.0 depending on the metal salt.

In addition to the at least three sequentially applied, preferably deposited, metal oxides, metal hydroxides and/or metal oxide hydrates, further metal oxides, metal hydroxides and/or metal oxide hydrates can of course be applied previously and/or subsequently, with the result that further layers can be arranged below or above the layer sequence [optional layer 1/2/spacer layer/layer 3].

During calcining, the metal ions present in layer B surprisingly presumably diffuse into layer A and/or layer C, forming mixed metal oxides and/or mixed metal hydroxides and/or metal oxide hydrates and/or mixtures of metal oxides and/or metal hydroxides and/or metal oxide hydrates in layer A and/or layer C. Because of the diffusion of the metal ions from layer B into layer A and/or layer C, during calcining layers 2 and 3 according to the invention, as well as the spacer layer in between are formed, wherein at least one of the two layers 2 and 3 comprises at least two different metal ions. Thus, from the originally three sequentially deposited layers A, B and C, during calcining layers 2 and 3 as well as the spacer layer in between are formed, wherein at least one of the two layers 2 and 3 comprises at least two different metal ions.

It is assumed that, among other things, the different mobility of the metal oxides, metal hydroxides and/or metal oxide hydrates relative to each other is responsible for the formation of the spacer layer during calcining. Here the mobility of the metal ions contained in layer B competes with the mobility of the metal ions contained in layers A and/or C, provided that the metal ions diffuse from layer B into at least one of the adjoining layers A and/or C and the metal ions from at least one of layers A and/or C diffuse into layer B. At present the inventors assume that, provided that the mobility of the metal ions contained in layer B during calcining is higher than the mobility of the metal ions contained in layers A and/or C, is one of the possible explanations for the formation of the spacer layer. In addition, it is assumed that a concentration gradient with respect to the metal ions favors the formation of a spacer layer, i.e. if more mobile metal ions from layer B can diffuse into one of the adjoining layers A and/or C than the other way round. In summary, it has been established that the formation of a spacer layer is caused during the calcining by a complex interaction of very widely varying further factors, such as for example entropic and/or enthalpic effects, which however have not yet been finally clarified. For the formation of at least one further spacer layer, the above considerations of course apply correspondingly.

In a preferred embodiment, the first and the third of the three sequentially applied, preferably deposited, metal oxides, metal hydroxides and/or metal oxide hydrates comprise at least one metal ion, selected from the group of metals consisting of Ti, Sn and Zr. After application, the first and the third metal oxide, metal hydroxide and/or metal oxide hydrate produce layer A or layer C. The second of the three sequentially applied, preferably deposited, metal oxides, metal hydroxides and/or metal oxide hydrates produces layer 3 and comprises at least one metal ion, selected from the group of metals consisting of Fe, Sn, Zr and Ce, which is different from the metal ions of the metal oxides, metal hydroxides and/or metal oxide hydrates deposited for producing layer A and layer C. In layer A and layer C, the applied, preferably deposited, metal oxides, metal hydroxides and/or metal oxide hydrates can be identical to or different from each other with respect to the metal ion(s).

Alternatively the transparent effect pigments according to the invention can be produced as follows:

suspending the calcined, single- or multi-coated non-metallic platelet-shaped substrates in water at a temperature from a range of from 50° C. to 100° C., sequentially applying two non-calcined layers B and C in the form of metal oxides, metal hydroxides and/or metal oxide hydrates by sequentially adding two water-soluble metal salts, in each case with simultaneous addition of mineral base, wherein the first water-soluble metal salt—for producing layer B—with respect to the metal ion is different from the other water-soluble metal salt for producing layer C and the layer which directly adjoins layer B in the direction of the substrate, separating the coated substrates from the coating solution(s), optionally washing and/or optionally drying the coated substrates, calcining the coated substrates at temperatures from a range of from 600° C. to 1100° C., preferably from a range of from 625° C. to 930° C. and particularly preferably from a range of from 750° C. to 890° C., obtaining the transparent effect pigments according to the invention comprising at least one spacer layer.

The application, preferably deposition, of the respective metal oxides, metal hydroxides and/or metal oxide hydrates here is also preferably effected at a constant pH in a range of from pH 1.4 to 10.0 depending on the metal salt.

If is assumed that, during calcining, the metal ions present in layer B diffuse at least into layer C, forming mixed metal oxides and/or mixed metal hydroxides and/or metal oxide hydrates and/or mixtures of metal oxides and/or metal hydroxides and/or metal oxide hydrates in layer C. Because of the diffusion of the metal ions from layer B at least into layer C, during calcining, layer 3 according to the invention as well as the spacer layer are formed. Thus, from the originally two sequentially deposited layers B and C, during calcining, layer 3 as wall as the spacer layer are formed, wherein at least layer 3 comprises at least two different metal ions. Layer 2 is here already present. The outermost layer of the calcined single- or multi-coated non-metallic platelet-shaped substrate used as starting material is called layer 2.

In a particularly preferred embodiment, the two or three sequentially applied, preferably deposited, metal oxides, metal hydroxides and/or metal oxide hydrates for producing layers B and C or A, B and C, comprise no metal ion(s) selected from the group of metals consisting of Si, Mg and Al.

During the sequential application of two non-calcined layers B and C to an already coated and optionally calcined substrate, the layer to which layer B is applied, according to the invention, comprises a high-refractive-index metal oxide, metal hydroxide and/or metal oxide hydrate. During the sequential application of thee non-calcined layers A, B and C to an already coated and optionally calcined substrate, the layer to which layer A is applied, according to the invention, can comprise a high-refractive-index or a low-refractive-index metal oxide, metal hydroxide and/or metal oxide hydrate.

The above statements, are explained in more detail below by way of example with reference to different coatings.

If, for example, a water-soluble titanium(IV) salt, a water-soluble iron(III) salt and again a water-soluble titanium(IV) salt are added successively to a suspension of an optionally coated, non-metallic platelet-shaped substrate, during the concluding calcining, observed in the SEM polished cross-section starting from the substrate, following the optionally already present coating, a layer 2 comprising a metal oxide, metal hydroxide and/or metal oxide hydrate, wherein the metal ions of the metal oxide, metal hydroxide and/or metal oxide hydrate comprise or are titanium ions and/or iron ions, a spacer layer as well as a layer 3 comprising a metal oxide, metal hydroxide and/or metal oxide hydrate, wherein the metal ions of the metal oxide, metal hydroxide and/or metal oxide hydrate comprise or are titanium ions and/or iron ions, are formed. At least one of the layers a metal oxide, metal hydroxide and/or metal oxide hydrate, wherein the metal ions of the metal oxide, metal hydroxide and/or metal oxide hydrate comprise or are titanium ions and/or iron ions, contains an iron titanate, preferably pseudobrookite and/or pseudorutile. With respect to the quantifies used, the above statements also apply here to coloring and non-coloring metal ions.

If, for example, a water-soluble salt, a water-soluble tin(IV) salt and again a water-soluble titanium(IV) salt are added successively to a suspension of an optionally coated, non-metallic platelet-shaped substrate, during the concluding calcining, observed in the SEM polished cross-section starting from the substrate, following the optionally already present coating, a layer 2 comprising a metal oxide, metal hydroxide and/or metal oxide hydrate, wherein the metal ions of the metal oxide, metal hydroxide and/or metal oxide hydrate comprise or are titanium ions and/or tin ions, a spacer layer as well as a layer 3 comprising a metal oxide, metal hydroxide and/or metal oxide hydrate, wherein the metal ions of the metal oxide, metal hydroxide and/or metal oxide hydrate comprise or are titanium ions and/or tin ions, are formed.

If, for example, a water-soluble titanium(IV) salt is added to a suspension of an optionally coated, non-metallic platelet-shaped substrate, calcined after deposition of titanium dioxide, titanium hydroxide and/or titanium oxide hydrate, this product is again suspended after the calcining, and a water-soluble salt as well as again a water-soluble titanium (IV) salt are added successively, during the concluding recalcining, observed in the SEM polished cross-section starting from the substrate following the optionally already present coating as well as layer 2 comprising a metal oxide, metal hydroxide and/or metal oxide hydrate, wherein the metal ion of the meal oxide, metal hydroxide and/or metal oxide hydrate comprise or are at least titanium ions, a spacer layer as well as a layer 3 composing a metal oxide, metal hydroxide and/or metal oxide hydrate, wherein the metal ions of the metal oxide, metal hydroxide and/or metal oxide hydrate comprise or are titanium ions and/or tin ions, are formed.

If the transparent effect pigments according to the invention, in addition to the at least two or three sequentially applied, preferably deposited, metal oxides, metal hydroxides and/or metal oxide hydrates, have further layers comprising metal oxides, metal hydroxides and/or metal oxide hydrates, further spacer layers can also be formed within the further layers, provided that the method steps described above for the at least two or three sequentially applied, preferably deposited, metal oxides, metal hydroxides and/or metal oxide hydrates are followed.

The transparent effect pigments according to the invention can optionally be provided with at least one outer protective layer which further increases weather stability and/or chemical stability and/or reduces photoactivity. The UV resistance as well as the condensation water stability were determined according to the statements below in Sections IIj "UV resistance" and IIi "Condensation water test".

The optionally present protective layer comprises metal oxides, metal hydroxides and/or metal oxide hydrates, the metal ions of which are selected from the group of metals consisting of Ce, Cr, Al, Zr, Zn and mixtures thereof, are preferably selected from the group of metals Si, Ce, Al, Zr and mixtures thereof. Here the proportion of optionally present protective layer preferably lies in a range of from 0.1 wt.-% to 7.0 wt.-%, particularly preferably in a range of from 0.2 wt.-% to 5.2 wt.-% and quite particularly preferably in a range of from 0.3 wt.-% to 3.1 wt.-%, in each case relative to the total weight of the transparent effect pigment according to the invention.

The optionally present protective layer can in addition be surface-modified, for example by silanes. The silanes can have no functional binding group or one or more functional binding group(s). Silanes with at least one functional binding group are also called organofunctional silanes below.

For example, one or more silanes can be applied to this outer protective layer. The silanes can be alkyl silanes with branched or unbranched alkyl radicals with 1 to 24 C atoms, preferably 6 to 18 C atoms.

In a further preferred embodiment, the silane with no functional binding group is an alkyl silane. The alkyl silane preferably has the formula $R_{(4-z)}Si(X)_z$. Here, z is an integer from 1 to 3, R is a substituted or unsubstituted, unbranched or branched alkyl chain with 10 to 22 C atoms and X stands for a halogen and/or alkoxy group. Alkyl silanes with alkyl chains with at least 12 C atoms are preferred. R can also be bound cyclically to Si, wherein in this case z is usually 2.

In a further embodiment, at least one organofunctional silane which allows a chemical binding to a plastic, a binder of a varnish or a paint etc. can also be used for the surface modification. The functional groups of the organofunctional silane can also be called coupling groups or functional binding groups and are preferably selected from the group which consists of hydroxy, amino, acryl, methacryl, vinyl, epoxy, isocyanate, cyano and mixtures thereof.

The organofunctional silanes preferably used as surface-modification agents, which have suitable functional groups, are commercially available and are produced for example by Evonik and sold under the trade name "Dynasylan". Further products can be procured from Momentive (Silquest silanes) or from Wacker, for example standard and a silanes from the GENIOSIL product group. Examples of these are 3-methacryloxypropyltrimethoxysilane (Dynasylan MEMO Silquest A-174NT), vinyltri(m)ethoxysilane (Dynasylan VTMO and VTEO respectively, Silquest A-151 and A-171 respectively), methyltri(m)ethoxysilane (Dynasylan MTMS and MTES respectively), 3-mercaptopropyltrimethoxysilane (Dynasylan MTMO; Silquest A-189), 3-glycidoxypropyltrimethoxysilane (Dynasylan GLYMO, Silquest A-187), tris[3-(trimethoxysilyl)propyl]isocyanurate (Silquest Y-11597), bis[3-(triethoxysilyl)propyl)]tetrasulfide (Silquest A-1289), bis[3-(triethoxysilyl)propyldisulfide (Silquest A-1589), beta-(3,4-epoxycyclohexyl)ethyltrimethoxysilane (Silquest A-186), bis(triethoxysilyl)ethane (Silquest Y-9805), gamma-isocyanatopropyltrimethoxysilane (Silquest A-Link 35, GENIOSIL GF40), methacryloxymethyltri(m)ethoxysilane (GENIOSIL XL 33, XL 36), (methacryloxymethyl)(m)ethyldimethoxysilane (GENIOSIL XL 32, XL 34), (isocyanatomethyl)methyldimethoxysilane, (isocyanatomethyl)trimethoxysilane, 3-(triethoxysilyl)propylsuccinic anhydride (GENIOSIL GF 20), (methacryloxymethyl)methyldiethoxysilane, 2-acryloxyethylmethyldimethoxysilane, 2-methacryloxyethyltriethoxysilane, 3-acryloxypropylmethyldimethoxysilane, 2-acryloxyethyltrimethoxysilane, 2-methacryloxyethyltriethoxysilane, 3-acryloxypropyltrimethoxysilane, 3-acryloxypropyltripropoxysilane, 3-methacryloypropyltriethoxysilane, 3-methacryloypropyltriacetoxysilane, 3-methacryloxypropylmethyldimethoxysilane, vinyltrichlorosilane, vinyltrimethoxysilane (GENIOSIL XL 10), vinyltris(2-methoxyethoxy)silane (GENIOSIL GF 58), vinyltriacetoxysilane or mixtures thereof, 3-Methacryloxypropyltrimethoxysilane (Dynasylan MEMO, Silquest A-174NT), vinyltri(m)ethoxysilane (Dynasylan VTMO and VTEO respectively, Silquest A-151 and A-171 respectively), methyltri(m)ethoxysilane (Dynasylan MTMS and MTES respectively), beta-(3,4-epoxycyclohexyl)ethyltrimethoxysilane (Silquest A-186), bis(triethoxysilyl)ethane (Silquest Y-9805), gamma-isocyanatopropyltrimethoxysilane (Silquest A-Link 35, GENIOSIL GF 40), methacryloxymethyltri(m)ethoxysilane (GENIOSIL XL 33, XL 36), (methacryloxymethyl)(m)ethyldimethoxysilane (GENIOSIL XL 32, XL 34), 3-(triethoxysilyl)propylsuccinic anhydride (GENIOSIL GF 20), vinyltrimethoxysilane (GENIOSIL XL 10) and/or vinyltris(2-methoxyethoxy)silane (GENIOSIL GF 58) are preferably used as organofunctional silanes.

It is however also possible to apply other organofunctional silanes to the particles according to the invention or the pigments according to the invention.

Furthermore, it is possible to use aqueous pre-hydrolysates, for example commercially available from Degussa. These include, among others, aqueous aminosiloxane (Dynasylan Hydrosil 1151), aqueous amino/alkyl functional siloxane (Dynasylan Hydrosil 2627 or 2909), aqueous diamino functional siloxane (Dynasylan Hydrosil 2776), aqueous epoxy functional siloxane (Dynasylan Hydrosil 2926), amino/alkyl functional oligosiloxane (Dynasylan 1146), vinyl/alkyl functional oligosiloxane (Dynasylan 6598), oligomeric vinylsilane (Dynasylan 6490) or oligomeric short-chain alkyl functional silane (Dynasylan 9896).

In a preferred embodiment, the organofunctional silane mixture contains, in addition to at least one silane with no functional binding group, at least one amino functional silane. The amino function is a functional group which can enter into one or more chemical interactions with most groups present in binders. This can include a covalent bond, such as e.g. with isocyanate or carboxylate functions of the binder, or hydrogen bridge bonds such as with OH or COOR functions or also ionic interactions. An amino function is therefore very suitable for the purpose of chemically binding the pigment to different types of binder.

The following compounds are preferably taken for this: 3-aminopropyltrimethoxysilanes (Dynasylan AMMO; Silquest A-1110), 3-aminopropyltriethoxysilane (Dynasylan AMEO), [3-(2-aminoethyl)aminopropyl]trimethoxysilane (Dynasylan DAMO, Silquest A-1120), [3-(2-aminoethyl)aminopropyl]triethoxysilane, triamino functional trimethoxysilane (Silquest A-1130), bis(gamma-trimethoxysilylpropyl)amine (Silquest A-1170), N-ethyl-gamma-aminoisobutyltrimethoxysilane (Silquest A-Link 15), N-phenyl-gamma-amnopropyltrimethoxysilane (SilquestY-9669), 4-amino-3,3-dimethylbutyltrimethoxysilane (Silquest A-1637), ((cyclohexylamino)methyl)(diethoxy)methyl silane (GENIOSIL XL 924), N-cyclohexylaminomethyltriethoxysilane (GENIOSIL XL 926) N-phenylaminomethyltrimethoxysilane (GENIOSIL XL 973) or mixtures thereof.

In a preferred embodiment, the optionally present protective layer has the composition disclosed in the respective main claims of WO 2006/021386 A1, WO 2012/130897 A1 or WO 2014/053454 A1.

Furthermore, the transparent effect pigments according to the invention can be provided with a surface modification which for example makes it easier to incorporate the effect pigments in different media. When the transparent effect pigments according to the invention are used for example in powder coatings, the effect pigments preferably have one of the surface modifications disclosed in the main claims of EP 2 698 403 A1 or EP 2 576 702 A1. Alternatively, the transparent effect pigments according to the invention can have an outermost coating according to WO 2006/136435 A2, claim 32, which is preferably applied by the spray-drying method according to WO 2006/136435 A2, claim 1.

When the transparent effect pigments according to the invention are used in cosmetic formulations, they can for example be more easily incorporated in O/W, W/O or W/Si emulsion systems by means of a hydrophobic surface covering, e.g. with triethoxycaprylylsilane (INCI) and a longer-lasting emulsion stability can be achieved.

The transparent effect pigments according to the invention can also be used in mixtures with transparent and/or opaque (in)organic white, colored, black pigments and/or metal effect pigments and/or pearlescent pigments and/or fillers in the desired application in each case. The quantity in which the transparent effect pigments according to the invention are used depends on the respective application as well as an the optical effect to be achieved.

The transparent effect pigments according to the invention can be used in cosmetic formulations, plastics, films, textiles, ceramic materials, glasses, paints, printing inks, inks, varnishes and/or powder coatings. Furthermore, the transparent effect pigments according to the invention can also be used for functional applications, such as e.g. laser marking greenhouse films or agricultural films.

In cosmetic formulations, such as for example body powder, face powder, pressed or loose powder, powder cream, eye makeup such as eyeshadow, mascara, eyeliner, liquid eyeliner, eyebrow pencil, lip balm, lipstick, lip gloss, lip liner, hairstyling compositions such as hairspray, hair mousse, hair gel, hair wax, hair mascara, permanent or semi-permanent hair dyes, temporary hair dyes, skin care compositions such as lotions, gels, emulsions, nail varnish compositions, the transparent effect pigments according to the invention can be combined with raw materials, additives and active ingredients suitable for the respective application. The total concentration of transparent effect pigments according to the invention in the cosmetic formulation can be between 0.001 wt.-% for rinse-off products and 40.0 wt.-% for leave-on products, in each case to the total weight of the formulation.

In a further embodiment, the transparent offset pigments according to the invention can be present in compact particle form. By "compact particle form" is meant pallets in the form of preferably cylinders and/or beads. The cylinders here preferably have a diameter from a range of from 0.2 cm 4.2 cm, particularly preferably from a range of from 0.5 cm to 2.3 cm and quite particularly preferably from a range of from 0.7 cm to 1.7 cm and particularly a length from a range of from 0.2 cm to 7.1 cm, particularly preferably from a range of from 0.6 cm to 5.3 cm und quite particularly preferably from a range of from 0.6 cm to 3.7 cm. The heads preferably have a radius of ≤1 cm, particularly preferably from a range of from 0.2 cm to 0.7 cm and quite particularly preferably from a range of from 0.3 cm to 0.5 cm.

In a further embodiment, the present invention relates to a transparent effect pigment comprising a non-metallic platelet-shaped substrate, preferably a synthetic mica platelet or a glass platelet, and a coating applied thereto, wherein the coating comprises
a) optionally a layer 1 which comprises or consists of tin oxide, tin hydroxide and/or tin oxide hydrate,
b) a layer 2 comprising as least one metal oxide, metal hydroxide and/or metal oxide hydrate, wherein the metal ion comprises or is at least one metal ion selected from the group of metals consisting of Ti, Sn and Fe,
c) a layer 3 comprising at least one metal oxide, metal hydroxide and/or metal oxide hydrate, wherein the metal ion comprises or is of least one metal ion selected from the group of metals consisting of Sn, Zr and Fe,
wherein at least one of layers 2 or 3 comprises at least two different metal ions from the above-listed groups, wherein the proportion of coloring metal ions, in each case determined via XRF analysts and in each case calculated as elemental metal, lies in a range of from 0.05 wt.-% to 1.9 wt.-%, relative to the total weighs of the effect pigment, and layers 2 and 3 are interrupted by a spacer layer of average height $h_a$ from a range of from 19 nm to 65 nm.

In a further embodiment, the present invention relates to a transparent effect pigment comprising a non-metallic platelet-shaped substrate, preferably a synthetic mica platelet or a glass platelet, and a coating applied thereto, wherein the coating comprises
a) optionally a layer 1 which comprises or consists of tin oxide, tin hydroxide and/or tin oxide hydrate,
b) a layer 2 comprising at least one metal oxide, metal hydroxide and/or metal oxide hydrate, wherein the metal ion comprises or is at least one non-coloring metal ion, selected from the group of metals consisting of Ti, Sn and Zr,
c) a layer 3 comprising at least one metal oxide, metal hydroxide and/or metal oxide hydrate, wherein the metal ion comprises or is at least one non-coloring metal ion, selected from the group of metals consisting of Ti, Sn and Zr,
and at least one of layers 2 or 3 comprises at least two different metal ions from the above-listed groups, layers 2 and 3 are interrupted by a spacer layer, and wherein the effect pigments have a span ΔD from a range of from 0.8 to 1.9.

In a further embodiment, the present invention relates to a transparent effect pigment comprising a non-metallic platelet-shaped substrate, preferably a synthetic mica platelet or a glass platelet, and a coating applied thereto, wherein the coating comprises
a) optionally a layer 1 which composes or consists of tin oxide, tin hydroxide and/or tin oxide hydrate,
b) a layer 2 comprising at least one metal oxide, metal hydroxide and/or metal oxide hydrate, wherein the metal ion comprises or is at least one metal ion selected from the group of metals consisting of Ti, Fe, Sn and Zr,
c) a layer 3 composing at least one metal oxide, metal hydroxide and/or metal oxide hydrate, wherein the metal ion comprises or is at least one metal ion selected from the group of metals consisting of Ti, Fe, Sn and Zr,
and at least one of layers 2 or 3 comprise at least two different metal ions, wherein the proportion of coloring metal ions, in each case determined via XRF analysis and in each case calculated as elemental metal, lies in a range of from 0.01 wt.-% to 3.9 wt.-% in total, preferably in a range of from 0.1 wt.-% to 2.9 wt.-% in total, and quite particularly preferably in a range of from 0.7 wt.-% to 2.1 wt.-% in total, and layers 2 and 3 are interrupted by a spacer layer of average $h_a$ from a range of from 12 nm to 71 nm, preferably from a range of from 21 nm to 53 nm.

In a preferred embodiment the present invention rotates to a transparent effect pigment comprising a non-metallic platelet-shaped substrate, preferably a synthetic mice platelet or a glass platelet, and a coating applied thereto, wherein the coating comprises
a) optionally a layer 1 which tin oxide, tin hydroxide and/or tin oxide hydrate,
b) a layer 2 comprising at least one metal oxide, metal hydroxide and/or metal oxide hydrate, wherein the metal ion comprises or is at least one metal ion selected from the group of metals consisting of Ti, Fe, Sn and Zr,
c) a layer 3 comprising at least one metal oxide, metal hydroxide and/or metal oxide hydrate, wherein the metal ion comprises or is at least one metal ion selected from the group of metals consisting of Ti, Fe, Sn and Zr,
and at least one of layers 2 or 3 comprises at least two different metal ions from the above-listed groups, wherein the proportion of coloring metal ions, in each case determined via XRF analysis and in each case calculated as elemental metal, lies in a range or from 0.03 wt.-% to 2.1 wt.-% in total, preferably in a range of from 0.06 wt.-% to 1.4 wt.-%, in each case relative to the total weight of the effect pigment, layers 2 and 3 are interrupted by a spacer layer and the effect pigment has a chemical resistance with a ΔE of <3, preferably <2.

In a particularly preferred embodiment the present invention relates to a transparent effect pigment comprising a non-metallic platelet-shaped substrate, preferably a synthetic mica platelet or a glass platelet, and a coating applied thereto, wherein the coating comprises
a) optionally a layer 1 which comprises or consists of tin oxide, tin hydroxide and/or tin oxide hydrate,
b) a layer 2 comprising at least one metal oxide, metal hydroxide and/or metal oxide hydrate, wherein the metal ions comprise or are at least two metal ions selected from the group of metals consisting of Ti and Sn,
c) a layer 3 comprising at least one metal oxide, metal hydroxide and/or metal oxide hydrate, wherein the metal ions comprise or are at least two metal ions selected from the group of metals consisting of TI and Sn,
and layers 2 and 3 are interrupted by a spacer layer, wherein the coating composes further high- and/or low-refractive-index layers and the effect pigment comprises at least one further spacer layer, running substantially parallel to the surface of the non-metallic platelet-shaped substrate, of average height $h_a$ from a range of from 11 nm to 58 nm, preferably from a range of from 17 nm to 47 nm.

In a further embodiment, the present invention relates to a transparent effect pigment comprising a non-metallic platelet-shaped substrate, preferably a synthetic mica platelet or a glass platelet, and a coating applied thereto, wherein the coating has at least one spacer layer lying substantially parallel to the surface of the non-metallic platelet-shaped substrate and the effect pigment can be obtained by i) optionally applying a non-calcined tin oxide, tin hydroxide and/or tin oxide hydrate layer to the non-metallic platelet-shaped substrate, sequentially applying three non-calcined metal oxides, metal hydroxides and/or metal oxide hydrates, wherein the second of these three non-calcined metal oxides, metal hydroxides and/or metal oxide hydrates is different in terms of material from the others and produced such that it can diffuse into at least one of the other non-calcined metal oxides, metal hydroxides and/or metal oxide hydrates as well as calcining the product obtained in step at a temperature from a range of from 720° C. to 970° C.

In a quite particularly preferred embodiment, the present invention relates to a transparent effect pigment comprising a non-metallic platelet-shaped substrate, preferably a synthetic mica platelet or a glass platelet, and a coating applied thereto, wherein the coating has at least one spacer layer, lying substantial parallel to the surface of the non-metallic platelet-shaped substrate, of average height $h_a$ from a range of from 14 nm to 51 nm, and the effect pigment can be obtained by i) optionally applying a non-calcined tin oxide, tin hydroxide and/or tin oxide hydrate layer to the non-metallic platelet-shaped substrate using a water-soluble tin (IV) salt, ii) sequentially applying a first layer A using a water-soluble titanium(IV) salt, a second layer B using a water-soluble tin(IV) and/or iron(III) salt, a third layer C using a water-soluble titanium(IV) salt and iii) calcining the product obtained in step ii) at a temperature from a range of from 710° C. to 910° C.

In an embodiment, instead of the at least one metal oxide, metal hydroxide and/or metal oxide hydrate, the coating of the transparent effect pigments according to the invention comprises the corresponding metal suboxides, metal fluorides, metal nitrides, metal oxynitrides, metal oxyhalides and/or metal sulfides.

In an embodiment, the coating of the transparent effect pigments according to the invention comprises, in addition to the at least one metal oxide, metal hydroxide and/or metal oxide hydrate, at least one metal suboxide, fluoride, metal nitride, metal oxynitride, metal oxyhalide and/or metal sulfide.

The invention is explained in more detail below by means of some examples, but the examples do not limit the invention. All percentages are to be understood as wt.-%.

I Preparation of the Transparent Effect Pigments According to the Invention

EXAMPLE 1

200 g of glass platelet with a particle-size distribution according to MALVERN Mastersizer MS 2000: $D_{10}$=34 µm, $D_{50}$=57 µm, $D_{90}$=96 µm were suspended in 1300 ml of demineralized water and heated to 85° C. under turbulent stirring. The pH of the suspension was reduced to pH 2.2. By adding 75 g of a tin chloride solution with a concentration of c(Sn)=12 g/l a layer of tin oxide was deposited on the surface of the glass platelets.

The pH was then reduced to pH 2.0 with dilute HCl and a solution of 148 ml of TiCl$_4$ (200 g of TiO$_2$/l of demineralized water) was then dosed into the suspension. Completion of the addition was followed by 10 minutes of stirring, and the pH was then adjusted to pH 2.6. Then 8 ml of an aqueous iron chloride solution with a density of 1.25 g/cm$^3$ was dosed in. Completion of the dosing was followed by another 10 minutes of stirring and by adding 75 ml of tin chloride solution with a concentration of c(Sn)=12 g/l, a further thin layer of tin oxide was deposited on the pigment surface. Then 180 ml of a solution of TiCl$_4$ (200 g of TiO$_2$/l of demineralized water) was dosed into the suspension, 15 minutes after completion of the addition the suspension was filtered off and the filter cake washed. The filter cake was dried and calcined at 900° C. for 60 minutes. Extremely chromatic, high-gloss, transparent effect pigments with golden interference color were obtained.

EXAMPLE 2

200 g of synthetic mica platelets (fluorphlogopite platelets) with a particle-size distribution according to MALVERN Mastersizer MS 2000: $D_{10}$=10 µm, $D_{50}$=22 µm, $D_{90}$=40 µm were suspended in 1300 ml of demineralized water and heated to 85° C. under turbulent stirring. The pH of the suspension was reduced to pH 2.2. By adding 100 g of a tin chloride solution with a concentration of c(Sn)=12 g/l a layer of tin oxide was deposited on the surface of the synthetic mica platelets. The pH of the suspension was reduced to pH 1.9 and a solution of 400 ml of TiCl$_4$ (200 g of TiO$_2$/l of demineralized water) was then dosed into the suspension. Completion of the addition was followed by 10 minutes of stirring, and the pH was than adjusted to pH 2.6. Then 30 ml of an aqueous iron chloride solution with a density of 1.42 g/cm$^3$ was dosed in. Completion of the dosing was followed by 10 minutes of stirring, and 405 ml of a further solution of TiCl$_4$ (200 g of TiO$_2$/l of demineralized water) was dosed into the suspension. 15 minutes after completion of the addition the suspension was filtered off and the filter cake washed. The filter cake was dried and calcined at 850° C. for 60 minutes. Extremely chromatic, high-gloss, transparent effect pigments with blue interference color were obtained.

EXAMPLE 3

200 g of synthetic mica platelets (fluorphlogopite platelets) with a particle-size distribution according to MALVERN Mastersizer MS 2000: $D_{10}$=10 µm, $D_{50}$=22 µm, $D_{90}$=40 µm were suspended in 1300 ml of demineralized water and heated to 85° C. under turbulent stirring. The pH of the suspension was reduced to pH 2.2. By adding 100 g of a tin chloride solution with a concentration of c(Sn)=12 g/l a layer of tin oxide was deposited on the surface of the synthetic mica platelets. The pH of the suspension was reduced to pH 1.9 and a solution of 360 ml of TiCl$_4$ (200 g of TiO$_2$/l of demineralized water) was then dosed into the suspension. Completion of the addition was followed by 10 minutes of stirring, and the pH was than adjusted to pH 2.2. Then 1000 g of a tin chloride solution with a concentration of c(Sn)=12 g/l was dosed in. Completion of the dosing was followed by 10 minutes of stirring, and 400 ml of a further solution of TiCl$_4$ (200 g of TiO$_2$/l of demineralized water) was dosed into the suspension. 15 minutes after completion of the addition the suspension was filtered off and the filter cake washed. The filter cake was dried and calcined at 850° C. for 60 minutes. Extremely chromatic, high-gloss, transparent effect pigments with blue interference color were obtained.

EXAMPLE 4

200 g of synthetic mica platelets (fluorphlogopite platelets) with a particle-size distribution according to MALVERN Mastersizer MS 2000: $D_{10}$=10 μm, $D_{50}$=22 μm, $D_{90}$=40 μm were suspended in 1300 ml of demineralized water and heated to 85° C. under turbulent stirring. The pH of the suspension was reduced to pH 1.9 and a solution of 380 ml of TiCl$_4$ (200 g of TiO$_2$/l of demineralized water) was then dosed into the suspension. Completion of the addition was followed by 10 minutes of stirring, and the pH was then adjusted to pH 2.2. Then 150 ml of an aqueous zirconium tetrachloride solution (w(ZrCl$_2$)=20%) was dosed in. Completion of the dosing was followed by 20 minutes of stirring, and 390 ml of a further solution of TiCl$_4$ (200 g of TiO$_2$/l of demineralized water) was dosed into the suspension. 15 minutes after completion of the addition the suspension was filtered off and the filter cake washed. The filter cake was dried and calcined at 850° C. for 60 minutes. Extremely chromatic, high-gloss, transparent effect pigments with blue interference color were obtained.

EXAMPLE 5

200 g of glass platelets with a particle-size distribution according to MALVERN Mastersizer MS 2000: $D_{10}$=10 μm, $D_{50}$=20 μm, $D_{90}$=40 μm were suspended in 1000 ml of demineralized water and heated to 85° C. under turbulent stirring. The pH of the suspension was reduced to pH 2.2. By addition 75 g of a tin chloride solution with a concentration of c(Sn)=12 g/l a layer of tin oxide was deposited on the surface of the glass platelets.

The pH was then reduced to pH 2.0 with dilute HCl and a solution of 100 ml of TiCl$_4$ (200 g of TiO$_2$/l of demineralized water) was then dosed into the suspension. Completion of the addition was followed by 60 minutes of stirring, and the pH was then adjusted to pH 2.2. Then 500 ml of a tin chloride solution with a concentration of c(Sn)=12 g/l was dosed in. Completion of the dosing was followed by 10 minutes of stirring, and 140 ml of a further solution of TiCl$_4$ (200 g of TiO$_2$/l of demineralized water) was dosed into the suspension. 60 minutes after completion of the addition the suspension was filtered off and the filter cake washed. The filter cake was dried and calcined at 800° C. for 60 minutes. Extremely chromatic, high-gloss, transparent effect pigments with blue interference color were obtained.

EXAMPLE 6

100 g of the effect pigment obtained in Example 4 was suspended in 850 ml of demineralized water and heated to 85° C. under turbulent stirring. The pH was reduced to pH 4.2 with dilute hydrochloric acid. Then a solution of 0.93 g of Ce(NO$_3$)$_3$×6 H$_2$O dissolved in 40 ml of demineralized water was dosed in. Simultaneously, the pH was kept constant by adding a 10% NaOH solution dropwise. Complete addition of the solution was followed by one hour of stirring, and afterwards the pH was adjusted to pH 10 with dilute sodium hydroxide. Then 5.7 g of Dynasylan 1146 diluted with 24.3 g of demineralized water was added to the suspension, followed by 180 minutes of stirring, the suspension was filtered off and the filter cake subsequently washed with demineralized water. The filter cake was dried under vacuum at 95° C. Extremely chromatic, high-gloss, transparent effect pigments with blue interference color were obtained.

Comparison Example 1

Multilayer pigment with golden interference color based on natural mica platelets, coated with titanium dioxide, silicon dioxide, titanium dioxide, Timiron Splendid Gold, from Merck.

Comparison Example 2

Multilayer pigment with green interference color based on natural mica platelets, coated with titanium dioxide, silicon dioxide, titanium dioxide, Timiron Splendid Blue, from Merck.

Comparison Example 3

Effect pigment with blue interference color based on synthetic mica platelets, coated with titanium dioxide, SYMIC C261, from ECKART.

Comparison Example 4

Effect pigment with blue interference color based on natural mica platelets, coated with titanium dioxide, Pyrisima T40-23 SW Blue, from Merck.

Comparison Example 5

Multilayer pigment with blue interference color based on natural mica platelets, coated with titanium dioxide, silicon dioxide, titanium dioxide, Lumina Royal Blue, from BASF.

Comparison Example 6

Effect pigment with blue interference color based on natural mica platelets, coated with titanium dioxide, Iriodin 7225 Ultra Blue, from Merck.

II Characterization of the Transparent Effect Pigments According to the Invention as well as of the Pigments of the Comparison Examples IIa Particle-Size Measurement The size-distribution curve of the transparent effect pigments according to the invention as well as the pigments of the comparison examples was determined with Malvern's Mastersizer 2000 device according to the manufacturers instructions. For this, approximately 0.1 g of the respective pigment as aqueous suspension, without the addition of dispersion aids, was placed under constant stirring in the sample preparation cell of the measurement device by means of a Pasteur pipette and measured several times. The average values ware calculated from the individual measurement results. The evaluation of the scattered light signals was effected according to the Fraunhofer method.

By the "average particle size $D_{50}$" is meant within the framework of this invention the $D_{50}$ value of the cumulative frequency distribution of the volume-averaged size-distribution function, as obtained by laser diffraction methods. The $D_{50}$ value indicates that 50% of the pigments have a volume-averaged diameter which is equal to or smaller than the indicated value, for example 20 μm. Correspondingly, the $D_{10}$ or $D_{90}$ value indicates that 10% or 90% respectively of the pigments have a volume-averaged diameter which is equal to or smaller than the respective measured value.

The span ΔD, defined as $$\Delta D = \frac{D_{90} - D_{10}}{D_{50}},$$

indicates the width of the particle-size distribution. With regard to the optical appearance of the transparent effect pigments according to the invention, a smaller value of ΔD, i.e. a narrow span, is preferred.

TABLE 2

Particle sizes

| Example/Comparison example | D10 [μm] | D50 [μm] | D90 [μm] | Span |
|---|---|---|---|---|
| Example 1 | 28.1 | 53.0 | 92.7 | 1.219 |
| Example 2 | 12.2 | 22.6 | 39.9 | 1.228 |
| Example 3 | 12.5 | 23.0 | 40.4 | 1.217 |
| Example 4 | 11.9 | 22.4 | 39.9 | 1.247 |
| Example 5 | 9.3 | 21.0 | 43.0 | 1.608 |
| Example 6 | 13.0 | 22.6 | 38.6 | 1.135 |
| Comparison example 1 | 12.6 | 24.4 | 44.8 | 1.320 |
| Comparison example 2 | 8.4 | 18.9 | 38.2 | 1.580 |
| Comparison example 3 | 11.0 | 32.0 | 38.5 | 1.250 |
| Comparison example 4 | 9.7 | 16.7 | 28.6 | 1.132 |
| Comparison example 5 | 10.6 | 19.7 | 34.9 | 1.240 |

IIb Angle-Dependent Color Measurements

For measuring the color and lightness values, the effect pigments according to the invention, the pigments of the comparison examples and the non-metallic platelet-shaped substrates at a pigmentation level of 6 wt.-% (pigments) and 10 wt.-% (substrates) respectively, in each case relative to the total weight of the wet varnish, were stirred into a conventional nitrocellulose varnish (Erco bronze mixed varnish 2615e colorless; Maeder Plastiklack AG). The respective pigments or the respective non-metallic platelet-shaped substrates were taken and then dispersed in the varnish with a brush. The finished varnish was applied to a doctor-blade drawdown device (RK Print Coat Instr. Ltd. Citenco Printing Apparatus Model K 101) with a spiral blade in a wet-film thickness of 40 μm or 76 μm (Example 1) on black-white opacity charts (Byko-Chart 2853, Byk-Gardner) and then dried at room temperature. The selection of the spiral blade is made according to Table A depending on the $D_{50}$ value of the pigments or substrates to be applied in each case. With the BYK-mac multi-angle colorimeter (Byk-Gardner) the color values ware determined on a black background of the opacity chart at a constant angle of incidence of 45° (in accordance with the manufacturer's instructions) at different angles of observation relative to the grazing angle. For characterizing the color intensity, the chroma value $C^*_{15}$ was used, which was measured on the black background of the black-white opacity chart as a measurement angle of 15° from the grazing angle.

Strongly reflecting samples (ideally mirrors) reflect almost all of the incident light at the so-called grazing angle. The closer the varnish application is measured to the grazing angle, the stronger the interference color appears.

TABLE A

Wet-film thickness depending on the $D_{50}$ value of the pigments or substrates to be applied

| $D_{50}$ value | Spiral blade |
|---|---|
| <40 μm | 40 μm |
| 40 μm-85 μm | 76 μm |
| >85 μm | 100 μm |

TABLE 3

Color values at an angle of observation of 15° relative to the grazing angle

| Example/Comparison example | a* 15° (s)[1] | b* 15° (s) | C* 15° (s) |
|---|---|---|---|
| Example 2 | −9.10 | −44.71 | 45.63 |
| Example 3 | 3.84 | −46.22 | 46.38 |
| Example 5 | 6.49 | −46.09 | 46.54 |
| Comparison example 2 | 8.11 | −49.70 | 50.36 |
| Comparison example 3 | 3.30 | −39.93 | 40.06 |

[1]Measured on a black background of the black-white opacity chart.

At the higher $C^*_{15}$ values of Table 3, measured on a black background of the black-white opacity chart, the transparent offset pigments according to rise invention with blue interference color from Examples 2, 3 and 5 are visibly clearly more color-intensive than the pigment covered only with a single titanium dioxide layer with blue interference color from comparison example 3. Their optical impression is approximately comparable to that of a multilayer pigment with blue interference color from comparison example 2.

IIc Opacity Comparison

For determining the opacity quotient $D_q$, defined as $$D_q = \frac{L^{*25}_{black}}{L^{*25}_{white}},$$

the lightness values L*25° of the varnish applications from IIb were recorded with the BYK-mac multi-angle colorimeter (Byk-Gardner) at a measurement aegis of 25° on the black and on the white background of the black-white opacity chart. At a constant angle of incidence of 45°, the measurement geometry 25° relates to the difference relative to the grazing angle. The angle of observation is measured from the secular reflection in the illumination plane.

The effect pigments according to the invention have a high transparency. Their opacity quotient $D_q$ is preferably ≤0.55. The opacity quotient $D_q$ of the transparent effect pigments according to the invention of Examples 1 to 5, as shown by Table 4, is in each case clearly below 0.5.

IId Gloss Measurements

The gloss is a measure of the directed reflection. For determining the gloss, the varnish applications from IIb were measured on the white background of the black-white opacity chart using a Byk-Gardner Micro-Tri-Gloss gloss meter at a measurement angle of 60° relative to the vertical. The gloss values of the transparent effect pigments according to the invention as well as of the pigments of the comparison examples are listed in Table 4.

The transparent effect pigments according to the invention from Examples 1 to 5 partly show clearly higher gloss values than the pigment coated with a single layer from comparison example 3. The gloss values of the transparent effect pigments according to the invention are sometimes even clearly higher than those of the multilayer pigments with the structure high-refractive-index/low-refractive-index/high-refractive-index from comparison examples 2, 4 and 5.

IIe Effect Measurements

In order to objectively describe the optical effect of the transparent effect pigments according to the invention, effect measurements ware carried out with the BYK-mac spectrophotometer (Byk-Gardner) on the basis of the varnish applications from IIb (cf. Byk-Gardner, Catalogue "Qualitätskontrolle für Lacke und Kunststoffe" ["Quality control for varnishes and plastics"] 2011/2012, pages 97/98). The corresponding measurement values for the glitter intensity S_i, the glitter area S_a and the granularity G are summarized in Table 4.

TABLE 4

Effect measurements, opacity quotient and gloss values

| Example/<br>Comparison<br>example | S_i<br>15° (s)[1] | S_a 15° (s)[1] | G (s)[1] | $D_q$ 25° | Gloss<br>60° (w)[2] |
|---|---|---|---|---|---|
| Example 1 | 56.13 | 27.90 | 16.63 | 0.4070* | 109.1 |
| Example 2 | 7.03 | 26.22 | 5.75 | 0.4740 | 43.7 |
| Example 3 | 5.44 | 22.25 | 4.62 | 0.4018 | 44.0 |
| Example 4 | 8.06 | 28.05 | 7.12 | 0.4990 | 46.8 |
| Example 5 | 18.65 | 34.94 | 6.24 | 0.3028 | 58.9 |
| Comparison example 2 | 6.70 | 29.53 | 5.14 | 0.3671 | 42.4 |
| Comparison example 3 | 4.69 | 20.65 | 4.14 | 0.3800 | 39.5 |
| Comparison example 4 | 4.70 | 21.22 | 3.13 | 0.3788 | 33.2 |
| Comparison example 5 | 4.52 | 21.80 | 3.58 | 0.3717 | 33.0 |
| Nitrocellulose varnish on black-white opacity chart | / | / | / | 0.1130 | 92.1 |

[1]Measured on a black background of the black-white opacity chart.
[2]Measured on a white background of the black-white opacity chart.
*76 μm wet film thickness The effect values S_i, S_a as well as G of the transparent effect pigments according to the invention from Examples 1 to 5 are either higher than or at least comparable to the values of comparison examples 2 to 5. Here too it can very easily be recognized that the achievable optical effects are clearly better than in the case of conventional pigments coated with a single layer from comparison examples 3 and 4. Even in comparison with the multilayer pigments from comparison examples 2, 4 and 5, the optical effects are at least equivalent, but usually better.

IIf Waring Blender Test

In the industry, many varnishes are processed in circulatory systems. Here the varnish components are exposed to high shear forces. The Waring Blender Test now simulates these conditions and serves to assess the ring-circuit or the shear stability. In this test, precisely pigments the coating of which is not sufficiently anchored to the carrier material show strong deviations of the chroma values compared with the untreated applications. The Waring Blender Test can thus be understood as a measure for the adhesion of the pigment coating vis-à-vis shear forces.

For this, the transparent effect pigments according to the invention or the pigments of the comparison examples were weighed in according to the following batch and mixed to a paste stepwise with a conventional acrylic varnish in an 880-ml beaker. The viscosity was then adjusted to 17" in a DIN 4-mm beaker with butyl acetate/xylene 1:1. In total 600 g of varnish was produced, 400 g of which was poured into a double-walled 1-kg container with water cooling and stirred using a Dispermat (Waring Blender) with a special attachment. The stirring time was 8 minutes at 13,500 rpm then 200 g of varnish was removed and the remainder was stirred for another 12 minutes.

Batch: 6% pigment
  8% butyl acetate 85
  86% acrylic varnish, colorless
  30% dilution butyl acetate 85/xylene 1:1

In each case 200 g of the untreated and of the treated varnish were applied to a test plate with an automatic spraying system and the Sata LP-90 spray gun according to the following setting.

Setting: Needle: 1.3.4
  Pressure: 4 bar
Coats: The number of spray coats was selected such that there was a dry varnish layer thickness of 15-20 μm.

Conventionally, effect pigments are regarded as shear-stable when, in the application according to the Waring Blender Test, the gloss and also the color difference, measured close to the grazing angle, are relatively small. The ΔC* 15° value relative to the untreated sample should ideally be less than 2.

Table 5 shows the color change ΔC* 15° as well as the gloss change Δgloss 60° of the sample subjected to the Waring Blender Test relative to the untreated sample on the basis of Example 4 according to the invention.

TABLE 5

Gloss and color difference in the Waring Blender Test

|  | ΔC* 15° | ΔGloss 60° |
|---|---|---|
| Example 4 | 1.1 | −1.0 |

The test plate of Example 4 according to the invention thus meets the test criteria. The color difference is negligibly small and scarcely perceptible to the naked eye. Even under a light microscope, changes such as flaking of the coating or other surface defects that had occurred could scarcely be detected. The transparent effect pigments according to the invention appear extremely shear-stable despite their spacer layer.

IIg Determination of the Chemical Resistance

The chemical resistance of the transparent effect pigments according to the invention and of the pigments of the comparison examples was determined on the basis of applications of varnish to plastic panels. 6 g of the respective pigment was stirred into a mixture of 90 g of a conventional colorless acrylic varnish and 10 g of butyl acetate 85. The viscosity was than adjusted to 17" in a DIN 4-mm beaker with a mixture of butyl acetate 85 and xylene in the ratio of 1:1.

In each case 100 g of this varnish was applied with an automatic spray system analogously to IIf covering the panels. After the coating the panels were stoved at 80° C. for 30 minutes. 24 hours later the panels were immersed halfway in 10% sodium hydroxide. After a residence time of 7 days, the panels were washed with demineralized water and then after 2 hours' drying time visually assessed for damage and/or discolorations. Furthermore, discolorations were measured using the BYK-mac (Byk-Gardner). For characterizing the color change, the ΔE value of the loaded sample was used, against the corresponding unloaded sample, at a measurement angle of 15°. The results are reproduced in Table 6 below.

TABLE 6

Color change ΔE

| Example/Comparison example | ΔE (15°) |
|---|---|
| Example 3 | 0.3 |
| Example 4 | 0.9 |
| Comparison example 1 | 9.3 |
| Comparison example 2 | 19.9 |
| Comparison example 5 | 59.8 |

Pigments with an ΔE (15°)<3 can be regarded as chemically stable. The transparent effect pigments according to the invention from Examples 3 and 4 lie clearly below this, while the pigments of comparison examples 1, 2 and 5 clearly exceed the limit value.

IIh X-Ray Fluorescence (XRF) Analysis

The metal oxide, metal hydroxide and/or metal oxide hydrate contents of the transparent effect pigments according to the invention as well as of the pigments of the comparison examples were determined by means of X-ray fluorescence (XRF) analysis. For this, the respective pigments ware incorporated into a lithium tetraborate glass tablet, fixed in solid sample measuring beakers and measured therefrom. Thermo Scientific's Advantix ARL device was used as measuring device. The measured values are reproduced in Table 7. The values of the different contents were indicated as $TiO_2$ for titanium, as $Fe_2O_3$ for iron, as $ZrO_2$ for zirconium and as $SnO_2$ for tin.

TABLE 7

Height $h_a$ of the spacer layer and XRF analysis values

| Example/ Comparison example | $h_a$ [nm] from SEM | XRF analysis (as metal oxide) | | | |
|---|---|---|---|---|---|
| | | Ti [%] | Fe [%] | Sn [%] | Zr [%] |
| Example 1 | 20 | 28.6 | 3.1 | 0.98 | / |
| Example 2 | 18 | 48.4 | 2.8 | 0.84 | / |
| Example 3 | 18 | 45.1 | 0.04 | 5.40 | / |
| Example 4 | 20 | 40.4 | 0.4 | / | 5.7 |
| Example 5 | 13 | 22.0 | / | 1.60 | / |
| Comparison example 1 | No spacer layer | 52.8 | 0.6 | / | / |
| Comparison example 2 | No spacer layer | 60.9 | / | / | / |
| Comparison example 3 | No spacer layer | 52.6 | 0.05 | 0.53 | / |
| Comparison example 4 | No spacer layer | 43.4 | 0.8 | 7.7 | / |
| Comparison example 5 | No spacer layer | 33.1 | 1.4 | 1.9 | / |

IIi Condensation Water Test

For determining the condensation-water resistance, the transparent effect pigments according to the invention or the pigments of the comparison examples were incorporates into a water varnish system and the test applications were produced by spray painting on aluminum sheets. The base coat was painted over with a commercially available 1K clear varnish and then stoved. These applications were tested according to DIN EN ISO 6270-2 "Paints and varnishes—Determination of resistance to humidity—Part 2: Procedure for exposing test specimens in condensation-water atmospheres" (ISO 6270-2:2006). The adhesive strength was tested by means of the cross-cut test according to DIN EN ISO 2409 "Paints and varnishes—Cross-cut test" (ISO 2409: 2013) immediately after the end of the last in comparison with the unloaded sample. Here Gt 0 means no change and Gt 5 means a very significant change.

The swelling behavior was visually assessed immediately after condensation-water loading according to DIN EN ISO 4628-1 "Paints and varnishes—Evaluation of degradation of coatings—Designation of quantity and size of defects, and of intensity of uniform changes in appearance—Part 1: General introduction and designation system" (ISO 4628-1:2003). Here the code number 0 means no change and 5 means a very significant change.

Finally the DOI (distinctness of image) was determined on the basis of a wave-scan II (Byk-Gardner).

TABLE 8

Condensation water results

| Example/ Comparison example | Gloss 20° before CW test | Gloss 20° after CW test | Loss of gloss | DOI | Cross-cut test immediately | Swelling visually |
|---|---|---|---|---|---|---|
| Example 6 | 91.2 | 90.8 | <1% | 80.4 | 0 | 0 |
| Comparison example 6 | 90.3 | 62.1 | 31% | 56.8 | 3 | 4 |

The pigment from comparison example 6 exhibited a strong swelling behavior and poor inter-layer adhesion. The transparent effect pigment according to the invention from Example 6 on the other hand appeared stable and exhibited almost no changes before and after the test.

IIj UV Resistance

The UV resistance of the transparent effect pigments according to the invention as well as of the pigments of the comparison examples was determined according to the UV rapid test described in EP 0 870 730 A1 for determining the photochemical UV activity of $TiO_2$ pigments. For this, 1.0 g of the corresponding pigment was dispersed in 9.0 g of a melamine-containing varnish rich in double-bonds. Doctor-blade drawdowns were prepared on white card and dried at room temperature. The doctor-blade drawdowns were divided and in each case one of the two sections was stored in the dark as an unloaded reference sample. The samples were then irradiated for 150 minutes in a QUV device from Q-Panel with UV-containing light (UVA-340 lamp, irradiance 1.0 W/m²/nm). Immediately after the end of the test, color values of the loaded samples were determined with a CM-508i colorimeter from Minolta relative to the respective retention sample. The resulting $\Delta E^*$ values, calculated according to the Hunter-L*a*b* formula, are shown in Table 9.

In this test, a substantially grey-blue discoloration of the $TiO_2$ layer of the respective pigment is observed because of Ti(III) species formed under UV light. A precondition for this is that the electron hole has spatially left the $TIO_2$ and—for instance by reaction with olefinic double bonds of the binder—cannot immediately recombine with the remaining electron again. As a melamine-containing varnish layer significantly slows down the diffusion of water (vapor) and oxygen at the pigment surface, the reoxidation of the titanium(III) species take place with a clear delay, with the result that the greying can be measured and the $\Delta E^*$ value can be used as a measure of the UV stability of the pigments. A larger $\Delta E^*$ numerical value of the loaded sample relative to the unloaded retention sample thus means a lower UV stability of the pigment examined.

TABLE 9

UV test results

| Example/Comparison example | $\Delta E^*$ |
|---|---|
| Example 6 | 3.7 |
| Comparison example 6 | 17.6 |

The pigment from comparison example 6 exhibited a clearly stronger color change ($\Delta E^*$) than Example 6 following corresponding exposure.

IIk Determination of the Average Thickness of the Non-Metallic Platelet-Shaped Substrates, the Average Layer Thickness of Layers 2 and 3, the Average Layer Thickness of the Entire Coating, the Average Height $h_a$ of the Spacer Layer as well as the Average Height $h_H$ of the Cavities For this, the transparent effect pigments according to the invention were incorporated 10% in a 2K clear varnish, Autoclear Plus HS from Sikkens GmbH, with a brush, applied to a film using a spiral blade (26 µm wet film thickness) and dried. After 24 hours' drying time, polished cross-sections were prepared from these doctor-blade drawdowns. The polished cross-sections were measured using SEM, wherein for determining the average thickness of the non-metallic platelet-shaped substrates at least 100 individual pigments were measured in order to obtain meaningful statistics. For determining the average layer thickness of layers 2 and 3, the average thickness of the entire coating, the average height $h_a$ of the spacer layer as well as the average height $h_H$ of the cavities, the upper and lower substrate surface, i.e. in each case the longer side of the non-metallic platelet-shaped substrate recognizable in the SEM polished cross-section, was in each case used as base line. The base line was here placed in the scanning electron microscope polished cross-section photograph along the surface of the platelet-shaped substrate in the polished cross-section photograph, by connecting the two intersections, non-metallic platelet-shaped substrate—optional and non-metallic platelet-shaped substrate—layer 2, to each other by a straight line from the left- and right-hand edge of the scanning electron microscope polishes cross-section photograph. The scanning electron microscope polished cross-section photographs ware examined using AxioVision 4.6.3. image-processing software (Zeiss).

At an angle of 90° to these two base lines, so many parallel lines were drawn in 50 nm apart that a grid was placed over the complete scanning electron microscope polished cross-section photograph of the effect pigment (FIG. 4). The magnification of the scanning electron microscope polished cross-section photograph was preferably at least 50,000 times, relative to Polaroid 545. Starting from the respective upper and lower base line of the non-metallic platelet-shaped substrate, in each case in the direction of layer 3 the distances between the intersections of these lines at the respective boundary surfaces of optional layer 1 to layer 2, layer 2 to the spacer layer, spacer layer to layer 3 and layer 3 to the environment ware measured manually. It occurred here that a line drawn in at a distance of 50 nm lay directly over a connection or a spacer. In this case only the respective intersection of the line at the boundary surface of layer 3 to the environment was recorded. From these measured values, the layer thicknesses of layers 2 and 3, the thickness of the entire coating, as well as the height $h_a$ of the spacer layer were obtained by subtraction.

The intersections of these parallel lines with the upper and lower cavity boundary within the spacer layer were used for determining the average height $h_H$ of the cavities.

From the individual values determined in this way of the lever thicknesses, the height $h_a$ as well as the height $h_H$, the respective arithmetic mean values were formed, in order to determine the above-indicated values of the average layer thicknesses, the average height $h_H$ or average height $h_a$. For meaningful statistics, the above-described measurements were carried out on at least 100 lines. By the term "average" is meant in all cases the arithmetic mean value.

Polishes cross-sections of the pigments of the comparison examples, which have not a spacer layer, but optionally statistically distributed pores within the coating, were also examined according to the above-described method on the basis of scanning electron microscope polished cross-section photographs. Here, if one of the parallel lines has come to lie over one or more pores, the height of the pore(s), their pore center(s) and the distance from the pore center or pore centers to the substrate surface were determined.

Alternatively to polished cross-sections, the transparent effect pigments according to the invention can be cut by means of the FIB (focused ion beam) method. For this, a fine beam of highly accelerated ions (e.g. gallium, xenon, neon or helium) is focused at a point by means of an ion-optical system and guided line by line over the effect pigment surface to be processed. The ions emit most of their energy on impact with the effect pigment surface and destroy the coating at this point, which leads to material removal line by line. Also, based on the scanning electron microscope photographs then taken, the average height $h_a$, the average layer thickness of layers 2 and 3 as well as the average layer thickness of the entire coating can be determined according to the method described above. Also, the average thickness of the non-metallic platelet-shaped substrate can be determined based on scanning electron microscope photographs of the effect pigments cut by the FIB method.

TABLE 10

Characterization of the coating

| Example/Comparison example | $d_{S2}$ [nm] | $d_{S3}$ [nm] | $d_{S2}/d_{S3}$ | $h_{ma}$ [nm] | $h_{Rma}$ | $\sigma h_{Rma}$ [%] | $n_S$ | $S_D$ [%] | $A_H$ [%] |
|---|---|---|---|---|---|---|---|---|---|
| Example 2 | 50 | 66 | 0.76 | 59.4 | 0.44 | 4.4 | 3.3 | 22.9 | 77.1 |
| Example 3 | 53 | 61 | 0.87 | 62.0 | 0.49 | 6.4 | 6.3 | 31.0 | 69.0 |
| Example 4 | 57 | 56 | 1.02 | 67.0 | 0.51 | 13.8 | 3.3 | 17.1 | 82.9 |
| Example 5 | 56 | 51 | 1.10 | 62.6 | 0.52 | 6.4 | 13.3 | 66.5 | 33.5 |
| Comparison example 3 | No spacer layer | | | | | 30.4 | 10 | 50.3 | 49.7 |

$d_{S2}$ [nm] = average layer thickness of layer 2
$d_{S3}$ [nm] = average layer thickness of layer 3
$h_{ma}$ = middle of the spacer layer (sum of the layer thickness of optional layer 1, layer 2 and half of height $h_a$)
$h_{Rma}$ = relative height of the spacer layer
$\sigma h_{Rma}$ [%] = standard deviation of the relative height of the spacer layer
$n_S$ = average number of bars per µm
$A_H$ [%] = surface area of cavity
$S_D$ = bar number density [%]

Table 7 shows the average height $h_a$ of the spacer layer of the measured pigments. All the transparent effect pigments according to the invention, unlike the pigments of comparison examples 1 to 6, have a spacer layer.

The pigment from comparison example 3 has no spacer layer, but statistically distributed pores within the coating (FIG. 5). In Table 10, for comparison example 3, by the value in the column $\sigma h_{Rma}$ [%] is meant the standard deviation of the pore centers relative to the substrate surface. As the pigment from comparison example 3 however only contains a few statistically distributed pores, the bar number density $S_D$ is 50.3%. The standard deviation of the pore centers relative to the substrate surface is 30.4%, proving that the pores are present statistically distributed within the entire coating. The case is different with the transparent effect pigment according to the invention from Example 5. Here too, at 66.5% the bar number density $S_D$ is very high, but the standard deviation of the relative height of the center of the spacer layer $h_{Rma}$ is 6.4%, which indicates that the spacer layer lies in a defined portion within the coating. The standard deviation of the distances from the pore centers to the substrate surface of the pigment from comparison example 3 can thus be contrasted with the standard deviation of the relative height of the center of the spacer layer of the transparent effect pigments according to the invention from Examples 2 to 5.

The spacer layer influences the optical properties of the transparent effect pigments according to the invention. In addition to high transparency, high gloss and high color intensity, the transparent effect pigments according to the invention have very good mechanical and chemical stability.

None of the pigments from the comparison examples exhibits the named properties in the overall view in a satisfactory manner.

III Scanning Electron Microscope Photographs

The scanning electron microscope photographs ware obtained on the basis of polished cross-sections of the transparent effect pigments according to the invention, with the Supra 35 scanning electron microscope (Zeiss) (for example FIGS. 1-4). The energy-dispersive X-ray microanalysis (EDX analysis) was carried out with the EDAX Sapphire device from EDAX.

III. Application-Specific Examples
Application-Specific Example 1: Body Lotion

| INCI Name | Product name | wt.-% | Manufacturer/Supplier |
|---|---|---|---|
| Phase A | | 85.80 | |
| | Effect pigment from Example 1 | 0.20 | |
| Aqua | Water | | |
| Glycerin | Glycerin 85% | 2.00 | H. Erhard Wagner |
| Xanthan Gum | Keltrol CG-T | 0.60 | CP Kelco |
| Phase B | | | |
| Isopropyl Palmitate | Isopropyl palmitate | 3.00 | H. Erhard Wagner |
| Glyceryl Stearate | Aldo MS K FG | 2.00 | Lonza |
| *Cocos Nuifera* Oil | Ewanol KR | 2.00 | H. Erhard Wagner |
| Cetearyl Alcohol | Tego Alkanol 1618 | 2.00 | Evonik |
| Dimethicone | Element 14 PDMS | 1.00 | Momentive |
| Sodium Polyacrylate | Cosmedia SP | 0.50 | BASF |
| Phase C | | | |
| Phenoxyethanol, Ethylhexylglycerin | Euxyl PE 9010 | 0.80 | Schülke & Meyr |
| Fragrance | Vitamin Bomb | 0.10 | Bell Europe |

The effect pigment from Example 1 can be used in a range of from 0.1 to 2.5 wt.-%, relative to the total weight of the body lotion formulation. The formulation can be made up to 100 wt.-% with water. Keltrol CG-T was dispersed in phase A and heated to 75° C. Phase B was separately heated to 75° C. Phase B was then slowly added to phase A. Under stirring, the emulsion was cooled to room temperature and phase C added individually.

Application-Specific Example 2: Cream Eyeshadow

| INCI Name | Product name | wt.-% | Manufacturer/Supplier |
|---|---|---|---|
| Phase A | | | |
| Microcrystalline Wax | TeCero-Wax 1030 K | 4.50 | Tromm Wachs |
| *Copernicia Cerifera* Cera | Carnauba wax LT 124 | 4.50 | Tromm Wachs |
| Isohexadecane | Isohexadecane | 21.00 | Ineos |
| Cyclopentasiloxane, Dimethicone/Vinyltrimethylsiloxysilicate Crosspolymer | Belsil RG 100 Silicone Elastomer Resin Gel | 8.00 | Wacker |
| Trimethylsiloxyphenyl Dimethicone | Belsil PDM 20 | 6.00 | Wacker |
| Dimethicone | Belsil DM 100 | 14.00 | Wacker |
| Caprylic/Capric Triglyceride | Miglyol 812 | 7.00 | Sasol |
| Cyclomethicone (and) Quaternium-90 Bentonite (and) Propylene Carbonate | Tixogel VSP-1438 | 5.00 | BYK |
| Phase B | | | |
| | Effect pigment from Example 5 | 30.00 | |

The effect pigment from Example 5 can be used in a range of from 5 to 30.0 wt.-%, relative to the total weight of the eyeshadow formulation. The formulation can be made up to 100 wt.-% with isohexadecane.

Phase A was mixed and heated to 85° C. phase B was then added to phase A under stirring. After being poured into a corresponding container the mixture is cooled to room temperature.

Application-Specific Example 3: Shower Gel

| INCI Name | Product name | wt.-% | Manufacturer/Supplier |
|---|---|---|---|
| Phase A | | | |
| | Effect pigment from Example 4 | 0.10 | |
| Aqua | Water | 58.50 | |
| Acrylates Copolymer | Carbopol Aqua SF-1 | 5.50 | Lubrizol |
| Phase B | | | |
| Sodium Hydroxide | NaOH (10 wt.-%) | 1.50 | |
| Phase C | | | |
| Sodium Laureth Sulfate | Zetesol NL-2 U | 22.00 | Zschimmer & Schwarz |
| Cocamidopropyl Betaine | Amphotensid B5 | 6.00 | Zschimmer & Schwarz |
| PEG-7 Glyceryl Cocoate | Emanon HE | 2.00 | Kao Corp. |
| Disodium Laureth Sulfosuccinate | Sectacin 103 special | 2.00 | Zschimmmer & Schwarz |
| Phase D | | | |
| Phenoxyethanol (and) Piroctone Olamine | Nipaguard PO 5 | 0.60 | Clariant |
| Fragrance | Water Lily OA | 0.20 | Bell Flavors and Fragrances |
| Sodium Chloride | Sodium Chloride | 1.60 | VWR |

The effect pigment from Example 4 can be used in a range of from 0.01 to 1.0 wt.-%, relative to the total weight of the shower gel formulation. The formulation can be made up to 100 wt.-% with water. Phase A was stirred, then phase B was added and stirred until a homogeneous appearance was achieved. Phase C was weighed in separately, briefly mixed and added to phase AB. Stirring was then resumed and phase D added individually.

Application-Specific Example 4: Pressed Eyeshadow

| INCI Name | Product name | wt.-% | Manufacturer/Supplier |
|---|---|---|---|
| Phase A | | | |
| Talc | Talc Powder | 36.00 | VWR |
| Bentonite | Optigel CK-PC | 5.00 | BYK |
| Synthetic Fluorphlogopite | Synafil S 1050 | 13.00 | ECKART |
| Aluminum Starch Octenylsuccinate | Agenaflo OS 9051 | 10.00 | Agrana |
| Magnesium Stearate | Magnesium Stearate | 6.00 | VWR |
| | Effect pigment from Example 3 | 20.00 | |
| Phase B | | | |
| Cyclomethicone | Xiameter PMX-0345 | 5.00 | Dow Corning |
| Octyldodecyl Stearoyl Stearate | Ceraphyl 847 | 5.00 | Ashland |

The effect pigment from Example 3 can be used in a range of 5.0 to 40.0 wt.-%, relative to the total weight of the eyeshadow formulation. The formulation can be made up to 100 wt.-% with talc.

Phase A was mixed at 2500 rpm in a high-speed mixer for 30 s. Phase B was then added and the mixture mixed at 3000 rpm in the same mixer for 60 s. Finally the powder mixture is pressed into shape by means of an eyeshadow press at 100 bar for 30 seconds.

Application-Specific Example 5: Mascara

| INCI Name | Product name | wt.-% | Manufacturer/Supplier |
|---|---|---|---|
| Phase A | | | |
| Aqua | Water | 73.00 | |
| Bentonite (and) Xanthan Gum | Optigel WX-PC | 2.00 | BYK |
| Phase B | | | |
| Cetyl Alcohol (and) Glyceryl Stearate (and) PEG-75 Stearate (and) Ceteth-20 (and) Steareth-20 | Emulium Delta | 5.00 | Gattefossé |
| C10-18 Triglycerides | Lipocire A Pellets | 2.00 | Gattefossé |
| Ozocerite | Kahlwax 1899 | 2.00 | Kahl |
| Glyceryl Behenate | Compritol 888 CG Pastilles | 2.00 | Gattefossé |
| Butylene Glycol Cocoate | Cocoate BG | 4.00 | Gattefossé |
| Phase C | | | |
| | Effect pigment from Example 1 | 5.00 | |
| Phenoxyethanol (and) Piroctone Olamine | Nipaguard PO5 | 0.50 | Clariant |
| *Glycine Soja* (Soybean) Oil, Dicaprylyl | Follicusan DP | 3.00 | CLR Berlin |

| INCI Name | Product name | wt.-% | Manufacturer/ Supplier |
|---|---|---|---|
| Ether, *Magnolia Grandiflora* Bark Extract, Lauryl Alcohol | | | |
| Water, Hydrolyzed Corn Starch, *Beta Vulgaris* (Beet) Root Extract | DayMoist CLR | 1.00 | CLR Berlin |
| Linoleic Acid (and) Linolenic Acid | Vitamin F forte | 0.50 | CLR Berlin |

The effect pigment from Example 1 can be used in a range of from 1.0 to 10.0 wt.-%, relative to the total weight of the mascara formulation. The formulation can be made up to 100 wt.-% with the water from phase A.

Phase A was stirred under high shear. Phase B was weighed in separately. Phase A and phase B were heated separately to 85° C., then phase B was added to phase A. Phase AB was then cooled to 45° C. and, during the cooling, phase C was added gradually under stirring.

Application-Specific Example 6: Hair Gel

| INCI Name | Product name | wt.-% | Manufacturer/ Supplier |
|---|---|---|---|
| Phase A | | | |
| Sodium Magnesium Silicate (nano) | Laponite XLG | 2.00 | BYK |
| Aqua | Water | 94.80 | |
| Phase B | | | |
| | Effect pigment from Example 1 | 0.10 | |
| Citric Acid (and) Water | Citric Acid (10%) | 0.30 | |
| Glycerin, Water, *Avena Strigosa* Seed Extract, Lecithin, Potassium Sorbate, Citric Acid | Aquarich | 1.50 | Rahn AG |
| Fragrance | Lychee & Grape | 0.10 | Bell Europe |
| Methylisothiazolinone (and) Phenethyl Alcohol (and) PPG-2 Methyl Ether | Optiphen MIT Plus | 1.20 | Ashland |

The effect pigment from Example 1 can be used in a range of from 0.01 to 2.0 wt.-%, relative to the total weight of the hair gel formulation. The formulation can be made up to 100 wt.-% with water.

The Laponite XLG was stirred with water until phase A became clear. The effect pigment from Example 1 was then added to phase B under stirring. The remaining ingredients were then gradually added to phase B.

Application-Specific Example 7: Body Powder

| INCI Name | Product name | wt.-% | Manufacturer/ Supplier |
|---|---|---|---|
| Phase A | | | |
| Synthetic Fluorphlogopite | Synafil S 1050 | 40.00 | Eckart |
| Polypropylene | Synafil W 1234 | 8.00 | Eckart |
| Bentonite | Optigel CK-PC | 10.00 | BYK |
| Talc | Talc Powder | 18.00 | VWR |
| Magnesium Stearate | Magnesium Stearate | 4.00 | Applichem |
| | Effect pigment from Example 1 | 20.00 | |

The effect pigment from Example 1 can be used in a range of from 0.2 to 5.0 wt.-%, relative to the total weight of the body power formulation. The formulation can be made up to 100 wt.-% with Synafil S 1050.

Phase A was mixed and then the powder was poured into a suitable container.

Application-Specific Example 8: Lip Gloss

| INCI Name | Product name | wt.-% | Manufacturer/ Supplier |
|---|---|---|---|
| Phase A | | | |
| Hydrogenated Polyisobutene (and) Ethylene/Propylene/Styrene Copolymer (and) Butylene/Ethylene/Styrene Copolymer | Versagel ME 750 | 75.30 | Penreco |
| *Simmondsia Chinensis* (Jojoba) Seed Oil | Jojoba Oil - Natural | 2.00 | BioChemica |

-continued

| INCI Name | Product name | wt.-% | Manufacturer/ Supplier |
|---|---|---|---|
| Caprylyl Trimethicone | Silcare Silicone 31M50 | 7.00 | Clariant |
| Stearyl Dimethicone | Silcare Silicone 41M65 | 3.20 | Clariant |
| Hydrogenated Polydecene | Dekanex 2004 FG | 4.00 | IMCD |
| Isopropyl Myristate | Isopropyl Myristate | 4.50 | VWR |
| Phase B | | | |
| | Effect pigment from Example 1 | 4.00 | |

The effect pigment from Example 1 can be used in a range of from 0.10 to 8.00 wt.-%, relative to the total weight of the lip gloss formulation. The formulation can be made up to 100 wt.-% with Versagel ME 750.

Phase A was heated to 85° C., then the effect pigment from Example 1 was added to phase B, stirred until a uniform consistency was formed and then poured into a lip gloss container.

Application-Specific Example 9: Lipstick

| INCI Name | Product name | wt.-% | Manufacturer/ Supplier |
|---|---|---|---|
| Phase A | | | |
| Octyldodecanol | Eutanol G | 42.5 | BASF |
| Candelilla Cera | Kahlwax 2039 | 6.00 | Kahl |
| *Copernicia Cerifera* (Carnauba) Wax | Kahlwax 2442 | 6.00 | Kahl |
| Bis-Diglyceryl Polyacyladipate-2 | Softisan 649 | 10.00 | Sasol |
| Polyisobutene | Rewopal PIB 1000 | 10.00 | Evonik |
| Hydrogenated Polydecene | Silkflo 364 NF polydecene | 5.00 | Ineos |
| C10-18 Triglycerides | Lipocire A Pellets | 5.00 | Gattefossé |
| *Acacia Decurrens*/Jojoba/ Sunflower Seed Wax/Polyglyceryl-3 Esters | Hydracire S | 5.00 | Gattefossé |
| Tocopheryl Acetate | dl-alpha-Tocopheryl Acetate | 0.50 | IMCD |
| Phase B | | | |
| | Effect pigment from Example 1 | 10.00 | |

The effect pigment from Example 1 can be used in a range of from 0.5 to 20.0 wt.-%, relative to the total weight of the lipstick formulation. The formulation can be made up to 100 wt.-% with Eutanol G.

Phase A was heated to 85° C., then phase B was added to phase A and mixed. This mixture was then poured into a lipstick mold at a temperature of 75° C.

Application-Specific Example 10: Liquid Eyeliner

| INCI Name | Product name | wt.-% | Manufacturer/ Supplier |
|---|---|---|---|
| Phase A | | | |
| Aqua | Water | 56.90 | |
| Bentonite (and) Xanthan Gum | Optigel WX-PC | 1.40 | |
| Phase B | | | |
| Lecithin | Emulmetik 100 | 0.10 | Lucas Meyer |
| *Copernicia Cerifera* Cera | Kahlwax 2442 | 1.00 | Kahl |
| Stearic Acid | Stearic Acid | 3.50 | Lipo Chemicals |
| Hydrogenated Polyisobutene | Panalane L14 E | 5.00 | Ineos |
| Polysorbate 60 | Mulsifan CPS 60 | 1.50 | Zschimmer & Schwarz |

-continued

| INCI Name | Product name | wt.-% | Manufacturer/Supplier |
|---|---|---|---|
| Phase C | | | |
| | Effect pigment from Example 3 | 4.00 | |
| Polyurethane-35 | Baycusan C 1004 | 18.00 | Bayer Cosmetics |
| Aqua and CI 77499 and Methylpropanediol and Ammonium Acrylates Copolymer and Simethicone and Caprylyl Glycol and Phenylpropanol Sodium Acrylates Copolymer | WorléeBase AQ 77499/1 | 8.00 | Worlée |
| Phenoxyethanol, Ethylhexylglycerin | Euxyl PE 9010 | 0.60 | Schülke & Mayr |

The effect pigment from Example 3 can be used in a range of from 0.5 to 8.0 wt.-%, relative to the total weight of the eyeliner formulation. The formulation can be made up to 100 wt.-% with water. Optigel WX-PC was dispersed in water of phase A and stirred for 10 minutes. Phase A and phase B were heated separately to 80° C. Phase B was then added slowly to phase A under stirring. After cooling to 45° C. the ingredients of phase C were added gradually and poured into suitable packaging.

Application-Specific Example 11: Mousse

| INCI Name | Product name | wt.-% | Manufacturer/Supplier |
|---|---|---|---|
| Phase A | | | |
| Cyclopentasiloxane | Xiameter PMX-0245 Cyclosiloxanes | 8.60 | Dow Corning |
| Hydrogenated Polyisobutene | MC 30 | 4.00 | Sophim |
| Dimethicone (and) Dimethicone Crosspolymer | Dow Corning 9041 Silicone Elastomer Blend | 37.14 | Dow Corning |
| Squalane | Squalane | 5.74 | Impag |
| Isononyl Isononanoate | Dermol 99 | 10.16 | Akzo International |
| Hydrogenated Jojoba Oil | Jojoba Butter LM | 2.15 | Desert Whale |
| Hydrogenated Jojaba Oil | Jojoba butter HM | 1.00 | Desert Whale |
| C30-45 alkyl methicone (and) C30-45 Olefin | Dow Corning AMS-C30 Cosmetic Wax | 1.15 | Dow Corning |
| Stearyl Dimethicone | Dow Corning 2503 Cosmetic Wax | 0.47 | Dow Corning |
| Cyclopentasiloxane (and) Polypropylsilsesquioxane | Dow Corning 670 Fluid | 5.00 | Dow Corning |
| Phase B | | | |
| Dimethicone/Vinyl Dimethicone Crosspolymer | Dow Corning 9506 Powder | 16.02 | Dow Corning |
| Silica Dimethyl Silylate | Covasilic 15 | 0.17 | LCW |
| Talc | Talc Powder | 5.00 | Sigma-Aldrich |
| | Effect pigment from Example 1 | 3.00 | |
| Phase D | | | |
| Phenoxyethanol, Ethylhexylglycerin | Euxyl PE 9010 | 0.40 | Schülke & Mayr |

The effect pigment from Example 1 can be used in a range of from 0.1 to 8.0 wt.-%, relative to the total weight of the mousse formulation. The formulation can be made up to 100 wt.-% with Dow Corning 9041 elastomer.

Phase A was mixed and heated until it was all melted. Phase B was weighed in separately and mixed with a high-speed mixer at 2400 rpm for 60 s. Half of the molten phase A was added to phase B and again mixed in the mixer at 2400 rpm for 30 s. The remainder of phase B was then also added to phase A and again mixed at 2400 rpm for 30 s. Finally, phase C is added to phase AB and again mixed in the high-speed mixer at 2400 rpm for 30 s.

Application-Specific Example 12: Nail Varnish

| INCI Name | Product name | wt.-% | Manufacturer/Supplier |
|---|---|---|---|
| Phase A | | | |
| | Effect pigment from Example 5 | 4.00 | |

-continued

| INCI Name | Product name | wt.-% | Manufacturer/Supplier |
|---|---|---|---|
| Phase B | | | |
| Butylacetate (and) Ethylacetate (and) Nitrocellulose (and) Isopropyl Alcohol | International Lacquers Nailpolish Base 15244 | 96.00 | International Lacquers |

The effect pigment from Example 5 can be used in a range of from 0.1 to 8.0 wt.-%, relative to the total weight of the nail varnish formulation. The formulation can be made up to 100 wt.-% with International Lacquers Nailpolish.

Phase A and phase B were mixed and then poured into a suitable container.

Application-Specific Example 13: Nail Varnish with "Soft Touch" Effect

| INCI Name | Product name | wt.-% | Manufacturer/Supplier |
|---|---|---|---|
| Phase A | | | |
| | Effect pigment from Example 2 | 4.00 | |
| Polypropylene | Synafil W 1234 | 5.00 | Eckart |
| Phase B | | | |
| Butylacetate (and) Ethylacetate (and) Nitrocellulose (and) Isopropyl Alcohol | International Lacquers Nailpolish Base 15244 | 91.00 | International Lacquers |

The effect pigment from Example 2 can be used in a range of from 0.1 to 8.0 wt.-%, relative to the total weight of the nail varnish formulation. The formulation can be made up to 100 wt.-% with International Lacquers Nailpolish.

Phase A was mixed, added to phase B and the nail varnish was then poured into a suitable container.

Application-Specific Example 14: Aqueous Nail Varnish

The pigments from Examples 1 to 6 can be used in an aqueous nail varnish according to WO 2007/115675 A2 Example 1. The pigmentation level here is 0.1 to 10.0 wt.-%, relative to the total weight of the formulation.

Application-Specific Example 15: Liquid Eyeshadow

| INCI Name | Product name | wt.-% | Manufacturer/Supplier |
|---|---|---|---|
| Phase A | | | |
| Water | Aqua | 73.80 | |
| Glycerin | Glycerin | 3.00 | H. Erhard Wagner |
| Phase B | | | |
| PEG-800 | Polyglycol 35000 S | 0.60 | Clariant |
| Ammonium Acryloyldimehtyltaurate/ VP Copolymer | Aristoflex AVC | 0.80 | Clariant |
| Acrylates Copolymer | Worlée Micromer CEK 20/50 | 5.00 | Worlée |
| Phase C | | | |
| | Effect pigment from Example 3 | 10.00 | |
| Divinyldimethicone/Dimethicone Copolymer C12-C13 Pareth-3, C12-C13 Pareth-23 | Dow Corning HMW 2220 Non-Ionic Emulsion | 6.00 | Dow Corning |
| Phenoxyethanol, Ethylhexylglycerin | Euxyl PE9010 | 0.80 | Schülke & Mayr |

The effect pigment from Sample 3 can be used in a range of from 0.10 to 20.00 wt.-%, relative to the total weight of the eyeshadow formulation. The formulation can be made up to 100 wt.-% with water.

Phase A was stirred, then the ingredients of phase B were added individually to phase A and stirred until a uniform consistency was formed. Then the ingredients of phase C were added individual to phase AB and stirred until a uniform consistency was formed again.

The invention claimed is:

1. A transparent effect pigment comprising a non-metallic platelet-shaped substrate and a coating applied to the substrate, wherein the coating comprises:
   a) optionally a layer 1 which comprises or consists of at least one of tin oxide, tin hydroxide or tin oxide hydrate,
   b) a layer 2 having a high refractive index n>1.8, the layer 2 comprising at least one of metal oxide, metal hydroxide or metal oxide hydrate, and
   c) a layer 3 having a high refractive index n>1.8, the layer 3 comprising at least one of metal oxide, metal hydroxide or metal oxide hydrate,
   and wherein at least one of layers 2 or 3 comprises at least two different metal ions and layers 2 and 3 are interrupted by a spacer layer formed between layers 2 and 3, wherein the spacer layer has connections in the form of bars arranged at an angle between 5 and 175 degrees to the non-metallic platelet-shaped substrate and cavities and wherein the transparent effect pigment is produced by a method comprising:
   (i) optionally applying a non-calcined layer, which comprises or consists of at least one of tin oxide, tin hydroxide or tin oxide hydrate, to the non-metallic platelet-shaped substrate,
   (ii) sequentially applying three non-calcined layers A, B and C, in each case made of or with at least one of metal oxide, metal hydroxide or metal oxide hydrate, wherein layers A, B and C are arranged directly on each other and wherein the at least one metal oxide, metal hydroxide and/or metal oxide hydrate applied in layer B, with respect to the metal ion, is different from the metal ion(s) of the metal oxides, metal hydroxides and/or metal oxide hydrates of layer A and layer C, (iii) calcining the product obtained in step (ii) at a temperature from a range of from 600° C. to 1000° C., obtaining the transparent effect pigment comprising at least one spacer layer, wherein the three sequentially applied metal oxides, metal hydroxides and/or metal oxide hydrates for producing layers A, B, and C do not comprise or are not a metal ion selected from the group of metals consisting of Si, Mg and Al, or by a method comprising:

(i) sequentially applying two non-calcined layers B and C, in each case made of or with at least one of metal oxide, metal hydroxide or metal oxide hydrate, to a calcined single- or multi-coated non-metallic substrate, wherein layers B and C are arranged directly on each other and wherein the at least one metal oxide, metal hydroxide and/or metal oxide hydrate applied in layer B, with respect to the metal ion, is different from the metal ion(s) of the metal oxide, metal hydroxide and/or metal oxide hydrate of layer C and the layer which directly adjoins layer B in the direction of the substrate, (ii) calcining the product obtained in step (i) at a temperature from a range of from 600° C. to 1000° C., obtaining the transparent effect pigment comprising at least one spacer layer, wherein the two sequentially applied metal oxides, metal hydroxides and/or metal oxide hydrates for producing layers B and C do not comprise or are not a metal ion selected from the group of metals consisting of Si, Mg and Al.

2. The transparent effect pigment according to claim 1, wherein the non-metallic platelet-shaped substrate is selected from the group consisting of natural mica platelets, synthetic mica platelets, glass platelets, $SiO_2$ platelets, $Al_2O_3$ platelets, kaolin platelets, talc platelets, bismuth oxychloride platelets and mixtures thereof, and the non-metallic platelet-shaped substrate is optionally coated with at least one of metal oxide, metal hydroxide or metal oxide hydrate and calcined.

3. The transparent effect pigment according to claim 1, wherein the effect pigment comprises further high- and low-refractive-index layers as well as optionally at least one further spacer layer.

4. The transparent effect pigment according to claim 1, wherein the at least two different metal ions of layer 2 and/or layer 3 are selected from the group of metals consisting of Ti, Fe, Sn, Mn, Zr, Ca, Sr, Ba, Ni, Sb, Ag, Zn, Cu, Ce, Cr and Co.

5. The transparent effect pigment according to claim 1, wherein the at least two different metal ions of layer 2 and/or 3 are selected from the group of metals consisting of Ti, Fe, Sn and Zr.

6. The transparent effect pigment according to claim 1, wherein a proportion of non-coloring metal ions selected from the group of metals consisting of Ti, Sn, Zr, Ca, Sr, Ba and Zn is >13 wt.-% in total, and a proportion of coloring metal ions selected from the group of metals consisting of Fe, Ti (II, III), Sn (II), Mn, Ni, Sb, Ag, Cu, Ce, Cr and Co is ≤4 wt.-% in total in the effect pigment, in each case determined by means of XRF analysis, in each case calculated as elemental metal and in each case relative to the total weight of the transparent effect pigment according to the invention.

7. The transparent effect pigment according to claim 1, wherein the at least one spacer layer is arranged substantially parallel to the surface of the non-metallic platelet-shaped substrate.

8. The transparent effect pigment according to claim 1, wherein the spacer layer in each case has an average height $h_a$ from a range of from 5 nm to 120 nm.

9. A method for producing the transparent effect pigment according to claim 1, wherein the method comprises:

(i) optionally applying a non-calcined layer, which comprises or consists of at least one of tin oxide, tin hydroxide or tin oxide hydrate, to the non-metallic platelet-shaped substrate, (ii) sequentially applying three non-calcined layers A, B and C, in each case made of or with at least one of metal oxide, metal hydroxide or metal oxide hydrate, wherein layers A, B and C are arranged directly on each other and wherein the at least one metal oxide, metal hydroxide and/or metal oxide hydrate applied in layer B, with respect to the metal ion, is different from the metal ion(s) of the metal oxides, metal hydroxides and/or metal oxide hydrates of layer A and layer C, (iii) calcining the product obtained in step (ii) at a temperature from a range of from 600° C. to 1000° C., obtaining the transparent effect pigment comprising at least one spacer layer.

10. A method for producing the transparent effect pigment according to claim 1, wherein the method comprises the following steps:

(i) sequentially applying two non-calcined layers B and C, in each case made of or with at least one of metal oxide, metal hydroxide or metal oxide hydrate, to a calcined single- or multi-coated non-metallic substrate, wherein layers B and C are arranged directly on each other and wherein the at least one metal oxide, metal hydroxide and/or metal oxide hydrate applied in layer B, with respect to the metal ion, is different from the metal ion(s) of the metal oxide, metal hydroxide and/or metal oxide hydrate of layer C and the layer which directly adjoins layer B in the direction of the substrate, (ii) calcining the product obtained in step (i) at a temperature from a range of from 600° C. to 1000° C., obtaining the transparent effect pigment comprising at least one spacer layer.

11. The method according to claim 9, wherein the metal ions contained in layer B diffuse, at least partially, into layer A and/or layer C, forming the at least one spacer layer in the calcined effect pigment.

12. The method according to claim 9, wherein the two or three sequentially applied metal oxides, metal hydroxides and/or metal oxide hydrates for producing layers B and C or layers A, B and C do not comprise or are not a metal ion selected from the group of metals consisting of Si, Mg and Al.

13. A process for producing a pigmented cosmetic formulation, plastic, film, textile, ceramic material, glass, paint, printing ink, ink, varnish, powder coating, coating composition or a material for a functional application comprising introducing the transparent effect pigment of claim 1 into a cosmetic formulation, plastic, film, textile, ceramic material, glass, paint, printing ink, ink, varnish, powder coating, coating composition or a material for a functional application.

14. An item comprising at least one transparent effect pigment according to claim 1.

15. The method according to claim 10, wherein the metal ions contained in layer B diffuse, at least partially, into layer A and/or layer C, forming the at least one spacer layer in the calcined effect pigment.

16. The process according to claim 13, wherein the functional application is laser marking, IR reflection, or photocatalysis.

17. A transparent effect pigment comprising a non-metallic platelet-shaped substrate and a coating applied to the substrate, wherein the coating comprises:
 a) optionally a layer 1 which comprises or consists of at least one of tin oxide, tin hydroxide or tin oxide hydrate,
 b) a layer 2 comprising at least one of metal oxide, metal hydroxide or metal oxide hydrate, and
 c) a layer 3 comprising at least one of metal oxide, metal hydroxide or metal oxide hydrate,
 and wherein at least one of layers 2 or 3 comprises at least two different metal ions and layers 2 and 3 are interrupted by a spacer layer formed between layers 2 and 3, wherein the spacer layer has connections in the form of bars arranged at an angle between 5 and 175 degrees to the non-metallic platelet-shaped substrate and cavities and wherein the spacer layer has a standard deviation of the relative height of $\sigma h_{Rma}$ in a range of 0.2 to 18%, wherein the relative height $h_{Rma}$ is defined as the ratio of the height $h_{ma}$ to the layer thickness of the overall coating and $h_{ma}$ refers to the sum total of the layer thickness of optional layer 1, layer 2 and half the height $h_a$ of the spacer layer.

18. A transparent effect pigment according to claim 17, wherein the mean height of the spacer layer is determined by the following method:
 the effect pigments are applied in a lacquer and cross sections are prepared and scanning electron micrographs analyzed thereof comprising the steps:
  establishing the upper and lower substrate surfaces as baselines which are the longer side of the nonmetallic substrate in platelet form in each case and drawing the baselines onto the scanning electron micrograph of the transverse section,
  analyzing the scanning electron micrographs of the transverse sections with the aid of the AxioVision 4.6.3 image processing software (from Zeiss),
  drawing a sufficient number of parallel lines at 50 nm intervals at a 90° angle with respect to the upper and lower baselines corresponding to the two surfaces of the substrate in platelet form establishing a grid over the effect pigment shown in the scanning electron micrograph of a transverse section (FIG. 4) using a magnification of at least 50 000-fold, based on Polaroid 545 (4"×5"),
  proceeding from the respective baseline of the nonmetallic substrate in platelet form, in the direction of the respective layer 3 or the respective outermost layer, the points of intersection between the parallel lines arranged at right angles to the respective baseline with the respective interfaces of the optional layer 1 with layer 2, of layer 2 with the spacer layer, of the spacer layer with layer 3, and of layer 3 with the environment or with any further layer applied, is recorded;
  determining the thicknesses of layers 2 and 3, the layer thickness of the overall coating, the layer thickness of further layers optionally present, and the height $h_a$ of the spacer layer by formation of differences, wherein the layer thickness of layer 2 is calculated from the difference between the respective measured points of intersection at the respective interfaces of layer 2 with the spacer layer and of either optional layer 1 or the baseline with layer 2 if the nonmetallic substrate has not been covered with further layers beforehand, and the layer thickness of layer 3 is calculated from the difference between the respective measured points of intersection at the respective interfaces of layer 3 with the environment or with any further layer applied and of the spacer layer with layer 3 and the height $h_a$ is calculated from the difference between the respective measured points of intersection of spacer layer with layer 3 and layer 2 with the spacer layer,
  wherein the height $h_a$ is determined by forming the arithmetic mean by conducting this procedure to at least 100 of the parallel lines arranged at right angles to the baselines.

19. A transparent effect pigment according to claim 17, wherein the standard deviation $\sigma h_{Rma}$ of the relative height is within a range from 0.3% to 15%.

20. A transparent effect pigment comprising a non-metallic platelet-shaped substrate and a coating applied to the substrate, wherein the coating comprises:
 a) optionally a layer 1 which comprises or consists of at least one of tin oxide, tin hydroxide or tin oxide hydrate,
 b) a layer 2 comprising at least one of metal oxide, metal hydroxide or metal oxide hydrate, and
 c) a layer 3 comprising at least one of metal oxide, metal hydroxide or metal oxide hydrate,
 and wherein at least one of layers 2 or 3 comprises at least two different metal ions and layers 2 and 3 are interrupted by a spacer layer formed between layers 2 and 3, wherein the spacer layer has connections in the form of bars arranged at an angle between 5 and 175 degrees to the non-metallic platelet-shaped substrate and cavities and wherein the spacer layer has a network density of <85%, wherein the network density is defined as the number of connections or spacers per number of lines in %, determined from a grid of parallel lines drawn at 50 nm intervals at a 90° angle from a baseline drawn onto each scanning electron micrograph of a traverse section along the surface of a longer side of the nonmetallic substrate.

21. A transparent effect pigment according to claim 20, wherein the network density of the spacer layer ranges from 1% to 75%.

22. The transparent effect pigment according to claim 17, wherein the non-metallic platelet-shaped substrate is selected from the group consisting of natural mica platelets, synthetic mica platelets, glass platelets, $SiO_2$ platelets, $Al_2O_3$ platelets, kaolin platelets, talc platelets, bismuth oxychloride platelets and mixtures thereof, and the non-metallic platelet-shaped substrate is optionally coated with at least one of metal oxide, metal hydroxide or metal oxide hydrate and calcined.

23. The transparent effect pigment according to claim 17, wherein the effect pigment comprises further high- and low-refractive-index layers as well as optionally at least one further spacer layer.

24. The transparent effect pigment according to claim 17, wherein the at least two different metal ions of layer 2 and/or layer 3 are selected from the group of metals consisting of Ti, Fe, Sn, Mn, Zr, Ca, Sr, Ba, Ni, Sb, Ag, Zn, Cu, Ce, Cr and Co.

25. The transparent effect pigment according to claim 17, wherein the at least two different metal ions of layer 2 and/or 3 are selected from the group of metals consisting of Ti, Fe, Sn and Zr.

26. The transparent effect pigment according to claim 17, wherein a proportion of non-coloring metal ions selected from the group of metals consisting of Ti, Sn, Zr, Ca, Sr, Ba and Zn is >13 wt.-% in total, and a proportion of coloring metal ions selected from the group of metals consisting of Fe, Ti (II, III), Sn (II), Mn, Ni, Sb, Ag, Cu, Ce, Cr and Co is ≤4 wt.-% in total in the effect pigment, in each case determined by means of XRF analysis, in each case calculated as elemental metal and in each case relative to the total weight of the transparent effect pigment according to the invention.

27. The transparent effect pigment according to claim 17, wherein the at least one spacer layer is arranged substantially parallel to the surface of the non-metallic platelet-shaped substrate.

28. The transparent effect pigment according to claim 17, wherein the spacer layer has an average height $h_a$ from a range of from 5 nm to 120 nm.

29. A method for producing the transparent effect pigment according to claim 17, wherein the method comprises:
   (i) optionally applying a non-calcined layer, which comprises or consists of at least one of tin oxide, tin hydroxide or tin oxide hydrate, to the non-metallic platelet-shaped substrate,
   (ii) sequentially applying three non-calcined layers A, B and C, in each case made of or with at least one of metal oxide, metal hydroxide or metal oxide hydrate, wherein layers A, B and C are arranged directly on each other and wherein the at least one metal oxide, metal hydroxide and/or metal oxide hydrate applied in layer B, with respect to the metal ion, is different from the metal ion(s) of the metal oxides, metal hydroxides and/or metal oxide hydrates of layer A and layer C,
   (iii) calcining the product obtained in step (ii) at a temperature from a range of from 600° C. to 1000° C., obtaining the transparent effect pigment comprising at least one spacer layer.

30. A method for producing the transparent effect pigment according to claim 29, wherein the method comprises the following steps:
   (i) sequentially applying two non-calcined layers B and C, in each case made of or with at least one of metal oxide, metal hydroxide or metal oxide hydrate, to a calcined single- or multi-coated non-metallic substrate, wherein layers B and C are arranged directly on each other and wherein the at least one metal oxide, metal hydroxide and/or metal oxide hydrate applied in layer B, with respect to the metal ion, is different from the metal ion(s) of the metal oxide, metal hydroxide and/or metal oxide hydrate of layer C and the layer which directly adjoins layer B in the direction of the substrate,
   (ii) calcining the product obtained in step (i) at a temperature from a range of from 600° C. to 1000° C., obtaining the transparent effect pigment comprising at least one spacer layer.

31. The method according to claim 29, wherein the metal ions contained in layer B diffuse, at least partially, into layer A and/or layer C, forming the at least one spacer layer in the calcined effect pigment.

32. The method according to claim 29, wherein the two or three sequentially applied metal oxides, metal hydroxides and/or metal oxide hydrates for producing layers B and C or layers A, B and C do not comprise or are not a metal ion selected from the group of metals consisting of Si, Mg and Al.

33. A process for producing a pigmented cosmetic formulation, plastic, film, textile, ceramic material, glass, paint, printing ink, ink, varnish, powder coating, coating composition or a material for a functional application comprising introducing the transparent effect pigment of claim 17 into a cosmetic formulation, plastic, film, textile, ceramic material, glass, paint, printing ink, ink, varnish, powder coating, coating composition or a material for a functional application.

34. An item comprising at least one transparent effect pigment according to claim 17.

35. The method according to claim 30, wherein the metal ions contained in layer B diffuse, at least partially, into layer A and/or layer C, forming the at least one spacer layer in the calcined effect pigment.

36. The process according to claim 33, wherein the functional application is laser marking, IR reflection, or photocatalysis.

37. The transparent effect pigment according to claim 20, wherein the non-metallic platelet-shaped substrate is selected from the group consisting of natural mica platelets, synthetic mica platelets, glass platelets, $SiO_2$ platelets, $Al_2O_3$ platelets, kaolin platelets, talc platelets, bismuth oxychloride platelets and mixtures thereof, and the non-metallic platelet-shaped substrate is optionally coated with at least one of metal oxide, metal hydroxide or metal oxide hydrate and calcined.

38. The transparent effect pigment according to claim 20, wherein the effect pigment comprises further high- and low-refractive-index layers as well as optionally at least one further spacer layer.

39. The transparent effect pigment according to claim 20, wherein the at least two different metal ions of layer 2 and/or layer 3 are selected from the group of metals consisting of Ti, Fe, Sn, Mn, Zr, Ca, Sr, Ba, Ni, Sb, Ag, Zn, Cu, Ce, Cr and Co.

40. The transparent effect pigment according to claim 20, wherein the at least two different metal ions of layer 2 and/or 3 are selected from the group of metals consisting of Ti, Fe, Sn and Zr.

41. The transparent effect pigment according to claim 20, wherein a proportion of non-coloring metal ions selected from the group of metals consisting of Ti, Sn, Zr, Ca, Sr, Ba and Zn is >13 wt.-% in total, and a proportion of coloring metal ions selected from the group of metals consisting of Fe, Ti (II, III), Sn (II), Mn, Ni, Sb, Ag, Cu, Ce, Cr and Co is ≤4 wt.-% in total in the effect pigment, in each case determined by means of XRF analysis, in each case calculated as elemental metal and in each case relative to the total weight of the transparent effect pigment according to the invention.

42. The transparent effect pigment according to claim 20, wherein the at least one spacer layer is arranged substantially parallel to the surface of the non-metallic platelet-shaped substrate.

43. The transparent effect pigment according to claim 20, wherein the spacer layer has an average height $h_a$ from a range of from 5 nm to 120 nm.

44. A method for producing the transparent effect pigment according to claim 20, wherein the method comprises:
   (i) optionally applying a non-calcined layer, which comprises or consists of at least one of tin oxide, tin hydroxide or tin oxide hydrate, to the non-metallic platelet-shaped substrate, (ii) sequentially applying three non-calcined layers A, B and C, in each case made of or with at least one of metal oxide, metal hydroxide or metal oxide hydrate, wherein layers A, B and C are arranged directly on each other and wherein the at least one metal oxide, metal hydroxide and/or metal oxide hydrate applied in layer B, with respect to the metal ion, is different from the metal ion(s) of the metal oxides, metal hydroxides and/or metal oxide hydrates of layer A and layer C, (iii) calcining the product obtained in step (ii) at a temperature from a range of from 600° C. to 1000° C., obtaining the transparent effect pigment comprising at least one spacer layer.

45. A method for producing the transparent effect pigment according to claim 20, wherein the method comprises the following steps:
(i) sequentially applying two non-calcined layers B and C, in each case made of or with at least one of metal oxide, metal hydroxide or metal oxide hydrate, to a calcined single- or multi-coated non-metallic substrate, wherein layers B and C are arranged directly on each other and wherein the at least one metal oxide, metal hydroxide and/or metal oxide hydrate applied in layer B, with respect to the metal ion, is different from the metal ion(s) of the metal oxide, metal hydroxide and/or metal oxide hydrate of layer C and the layer which directly adjoins layer B in the direction of the substrate, (ii) calcining the product obtained in step (i) at a temperature from a range of from 600° C. to 1000° C., obtaining the transparent effect pigment comprising at least one spacer layer.

46. The method according to claim 45, wherein the metal ions contained in layer B diffuse, at least partially, into layer A and/or layer C, forming the at least one spacer layer in the calcined effect pigment.

47. The method according to claim 44, wherein the two or three sequentially applied metal oxides, metal hydroxides and/or metal oxide hydrates for producing layers B and C or layers A, B and C do not comprise or are not a metal ion selected from the group of metals consisting of Si, Mg and Al.

48. A process for producing a pigmented cosmetic formulation, plastic, film, textile, ceramic material, glass, paint, printing ink, ink, varnish, powder coating, coating composition or a material for a functional application comprising introducing the transparent effect pigment of claim 20 into a cosmetic formulation, plastic, film, textile, ceramic material, glass, paint, printing ink, ink, varnish, powder coating, coating composition or a material for a functional application.

49. An item comprising at least one transparent effect pigment according to claim 20.

50. The method according to claim 45, wherein the metal ions contained in layer B diffuse, at least partially, into layer A and/or layer C, forming the at least one spacer layer in the calcined effect pigment.

51. The process according to claim 48, wherein the functional application is laser marking, IR reflection, or photocatalysis.

* * * * *

UNITED STATES PATENT AND TRADEMARK OFFICE
CERTIFICATE OF CORRECTION

PATENT NO. : 10,934,436 B2  
APPLICATION NO. : 15/536206  
DATED : March 2, 2021  
INVENTOR(S) : Michael Grüner et al.

Page 1 of 1

It is certified that error appears in the above-identified patent and that said Letters Patent is hereby corrected as shown below:

On the Title Page

Column 1, Assignee, Line 1, delete "GmbH" and insert -- GmbH, (DE) --

In the Claims

Column 53, Line 51, Claim 18, delete "50 000-fold," and insert -- 50,000-fold, --

Column 58, Line 1, Claim 46, delete "claim 45," and insert -- claim 44, --

Signed and Sealed this  
Tenth Day of August, 2021

Drew Hirshfeld  
*Performing the Functions and Duties of the*  
*Under Secretary of Commerce for Intellectual Property and*  
*Director of the United States Patent and Trademark Office*